United States Patent [19]
Chadhá et al.

[11] 3,933,892

[45] Jan. 20, 1976

[54] ASYMMETRIC SYNTHESIS OF OPTICALLY ACTIVE PROSTAGLANDINS

[75] Inventors: Naresh Kumar Chadha, Nutley; John Joseph Partridge, Jr.; Milan Radoje Uskokovic, both of Upper Montclair, all of N.J.

[73] Assignee: Hoffmann-La Roche Inc., Nutley, N.J.

[22] Filed: Jan. 18, 1974

[21] Appl. No.: 434,539

Related U.S. Application Data

[63] Continuation-in-part of Ser. No. 331,931, Feb. 12, 1973, abandoned.

[52] U.S. Cl..... 260/468 J; 260/343.3; 260/346.7 R; 260/348; 260/345; 260/456 R; 260/468 D; 260/468 K; 260/488 R; 260/511 D; 260/511 K; 260/580 R; 260/611 R; 260/617 R

[51] Int. Cl.$^2$............................................ C07F 5/02
[58] Field of Search ...................... 260/468 J, 514 J

[56] References Cited
OTHER PUBLICATIONS

House, Modern Synthetic Reactions pp. 106–116, (1972).
McOmie, Protective Groups in Organic Chemistry, pp. 204–208 (1973).

Primary Examiner—Robert Gerstl
Attorney, Agent, or Firm—Samuel L. Welt; Jon S. Saxe; William H. Epstein

[57] ABSTRACT

An asymmetric synthesis of optically active prostaglandin $F_2$ α from cyclopentadiene including intermediates in this synthesis.

3 Claims, No Drawings

ASYMMETRIC SYNTHESIS OF OPTICALLY ACTIVE PROSTAGLANDINS

CROSS REFERENCE TO RELATED APPLICATIONS

This application is a continuation-in-part application of U.S. Ser. No. 331,931, filed Feb. 12, 1973, Chadha et al now abandoned.

BACKGROUND OF THE INVENTION

Optically active prostaglandin $F_{2\alpha}$ has been isolated from natural sources. These compounds as well as the 15-eip-prostaglandin $F_{2\alpha}$ compounds are known agents for inducing labor in pregnant women and for the therapeutic termination of pregnancy.

In the past, racemic prostaglandin $F_{2\alpha}$ has been synthesized by Fried in the *Journal of American Chemical Society*, 94, 4342, 4343 (1972) and Corey, *Tetrahedron Letters*, 307, 311 (1970). While racemic prostaglandin is also active in inducing labor in pregnant women and terminating pregnancy, the racemic form of this compound is not as active as its optically active forms. Various procedures have been proposed for synthesizing the optically active forms of prostaglandin $F_{2\alpha}$ utilizing resolving techniques. However, these procedures have been uneconomical and cumbersome. Therefore, it has been desired to provide a direct asymmetric synthesis of optically active prostaglandin $F_{2\alpha}$ which avoids cumbersome resolution procedures.

SUMMARY OF THE INVENTION

In accordance with this invention, optically active prostaglandin $F_{2\alpha}$ which has the formula:

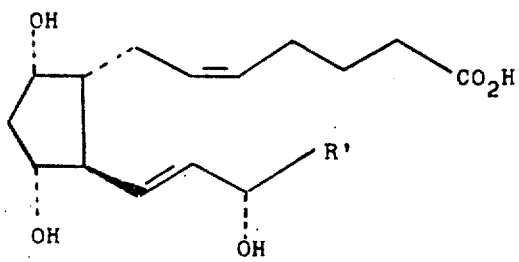

I wherein R' is $-CH_2-CH_2-CH_2-CH_2-CH_3$
as well as its optically active antipode which has the formula:

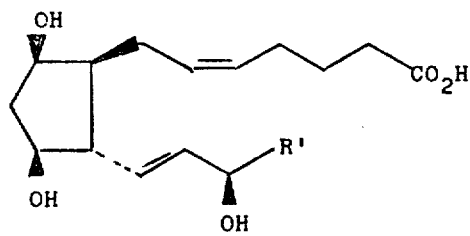

I-A wherein R' is as above;
and optically active 15-epi-prostaglandin $F_{2\alpha}$ which has the formula:

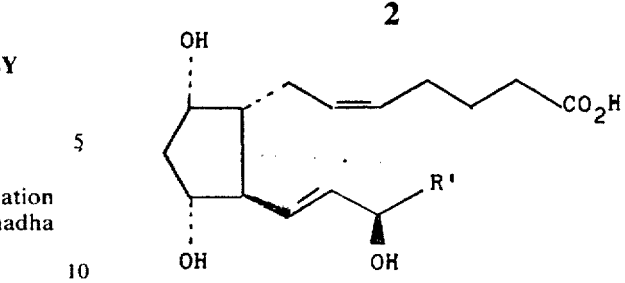

II wherein R' is as above;
as well as its optically active antipode which has the formula:

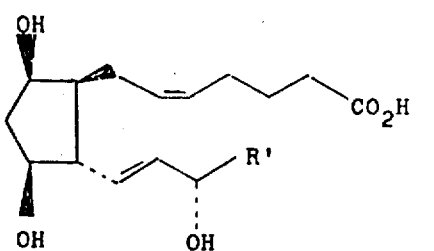

II-A wherein R' is as above;
can be asymmetrically synthesized from cyclopentadiene without cumbersome resolution procedures via optically active intermediates of the formulae:

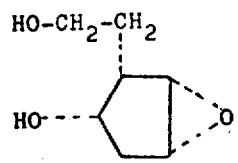

III and

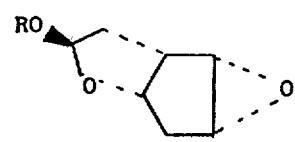

IV wherein —OR forms hydroxy protected with an ether protecting group convertible to hydroxy by hydrolysis;
or their optically active antipodes. By this process, either the optical isomer of formulae I or II or their optical antipodes, i.e., the compound of formulae I-A or II-A can be synthesized directly from cyclopentadiene depending upon the reaction conditions utilized without the necessity of resolution.

DETAILED DESCRIPTION OF THE INVENTION

As used throughout this application, the term "lower alkyl" includes both straight chain and branched chain alkyl groups having from 1 to 7 carbon atoms, such as methyl, ethyl and propyl, preferably methyl. As used herein, the term "lower alkoxy" comprehends lower alkoxy groups having from 1 to 7 carbon atoms such as methoxy and ethoxy. As also used herein, the term "lower alkanoic acids" comprehends an alkanoic acid of 2 to 7 carbon atoms such as propionic acid and acetic acid. As further used herein, the term "halogen" or "halo," unless otherwise stated, comprehends fluorine, chlorine, bromine and iodine. The term "alkali metal" includes sodium, potassium, lithium, etc.

In the pictorial representation of the compounds given throughout this application, a thickened tapered line (▼) indicates a substituent which is in the beta-orientation (above the plane of the cyclopentane moiety), a dotted line (---) indicates a substituent which is in the alpha-orientation (below the plane of the cyclopentane moiety) and a wavy line (~) indicates a substituent which is in either the alpha- or beta-orientation. It is to be understood that the pictorial representations of the structural formula represent absolute configuration unless otherwise stated. In many cases, for the sake of convenience, only one optically active antipode is pictorally represented. It is understood that the other optically active antipode has the same structural formula except that the dotted lines are tapered lines and tapered lines are dotted lines.

As also used herein, the term "aryl" signifies mononuclear aromatic hydrocarbon groups such as phenyl, tolyl, etc., which can be unsubstituted or substituted in one or more positions with an aryl, a lower alkylenedioxy, a halogen, a nitro, a lower alkyl or a lower alkoxy substituent, and polynuclear aryl groups such as naphthyl, anthryl, phenanthryl, azulyl, etc., which can be ubsubstituted or substituted with one or more of the aforementioned groups. The preferred aryl groups are the substituted and unsubstituted mononuclear aryl or diaryl groups, particularly phenyl or diphenyl. The term "aryl lower alkyl" comprehends groups wherein aryl and lower alkyl are defined as above, particularly benzyl. The term "aryl lower alkanoic acid" comprehends acids wherein "aryl" and "lower alkanoic acid" are as defined above, particularly phenyl acetic acid. The term "aroyl" denotes aroyl groups where the aryl group is defined as above. The preferred aroyl substituents are benzoyl or phenylbenzoyl.

As still further used herein, the term "carboxy protected with a group convertible thereto by hydrolysis" comprehends any conventional organic acid protecting group which can be removed by hydrolysis. The preferred organic acid protecting groups are the esters. Any conventional ester that can be hydrolyzed to yield the acid can be utilized as the protecting group. Exemplary esters useful for this purpose are lower alkyl esters, such as ethyl, aryl esters, particularly phenyl ester and the aryl lower alkyl esters, particularly benzyl ester or phenylbenzyl ester.

As used herein, the term "hydroxy protected by ester or either group convertible to hydroxy by hydrolysis" designates any ester or ether group which can be hydrolyzed to yield the hydroxy group. Exemplary ester groups useful for this purpose are those in which the acyl moiety is derived from a lower alkanoic, an aryl lower alkanoic, an aroic, a lower alkane dicarboxylic acid or a carbamic acid such as an aryl carbamic acid which includes phenyl carbamic acid or p-phenylphenyl carbamic acid. Among the acid derivatives which can be utilized to form such ester groups are the acid anhydrides and the acid halides, preferably chlorides or bromides, with the lower alkanoic acid anhydrides, e.g., acetic anhydride and caproic anhydride, the aryl lower alkanoic acid anhydrides, e.g., benzoic acid anhydrides, lower alkane dicarboxylic acid anhydrides, e.g., succinic anhydride, and chloroformates, e.g., trichloroethylchloroformate, being preferred. In preparing aryl carbamic acid ester, the free hydroxy group is reacted with an aryl isocyanate under conditions conventional for preparing acid esters. A suitable ether protecting group is, for example, lower alkyl ethers such as methyl, ethyl or t-butyl ethers, tetrahydropyranyl ether or 4-methoxy-5,6-dihydro-2H-pyranyl ether. Others are arylmethyl ethers such as benzyl, benzhydryl, or trityl ethers or alpha-lower alkoxy lower alkyl ethers, for example, methoxymethyl or allylic ethers, or tri(lower alkyl) silyl ethers such as trimethyl silyl ether.

In the first step of the process of this invention, the alkali metal and thallium (I) salts of cyclopentadiene are reacted with a compound of the formula:

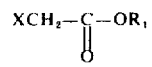

wherein

forms an ester protecting group convertible to carboxy by hydrolysis and X is halogen; to form a compound of the formula:

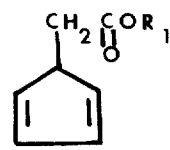

VI wherein $R_1$ is as above. The compound of formula V is reacted with the alkali metal or thallium (I) salts of cyclopentadiene in an inert organic solvent. The preferred inert organic solvents for carrying out this reaction are the ether solvents such as tetrahydrofuran, diethyl ether, glyme, diglyme, triglyme, tetraglyme, etc. In carrying out this reaction, any temperature of from −100°C. to room temperature can be utilized. Generally, it is preferred to utilize a temperature of from −90°C. to −20°C.

In the next step of the process of this invention, the compound of formula VI is converted to the optically active isomer of the formula:

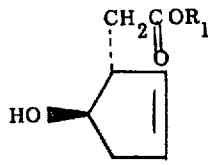

VII wherein $R_1$ is as above;
by first reacting the compound of formula VI with an optically active organo boron hydride to produce an optically active isomer of the formula:

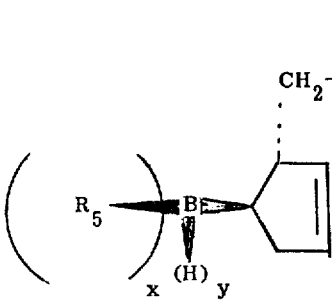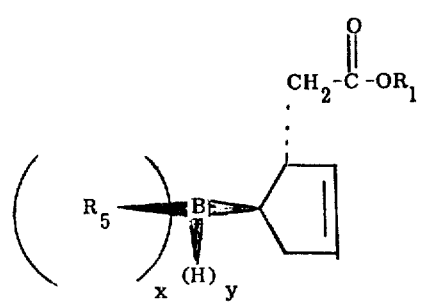

VIII-A wherein $R_5$ is an optically active organo moiety; $R_1$ is as above; x is an integer of from 1 to 2; y is an integer from 0 to 1 with the proviso that the sum of x and y is 2;

or an optically active isomer of the formula:

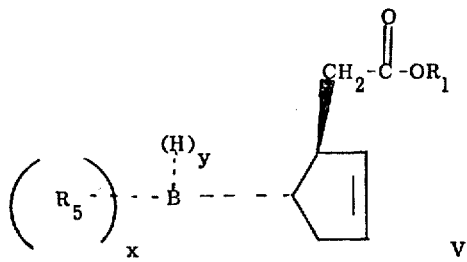

VIII-B wherein x, y, $R_1$ and $R_5$ are as above.

The compound of formula VIII-A can be converted to the compound of formula VII whereas the compound of formula VIII-B can be converted to the optically active isomer of the formula:

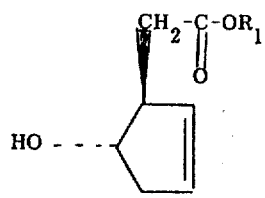

VII-A wherein $R_1$ is as above;
by treatment with an alkali metal hydroperoxide or a perorganic acid.

Any conventional optically active organo boron hydride can be utilized to convert the compound of formula VI to a compound of formula VIII-A or a compound of formula VIII-B. Among the preferred organo boron hydrides are those which are disubstituted with an optically active organo moiety ($R_5$) which is an optically active hydrocarbyl group. These disubstituted organo hydroborans are formed as described in U.S. Pat. No. 3,078,313, Feb. 19, 1963, Brown, by hydroboration of an optically active olefinic hydrocarbon. Among the optically olefinic hydrocarbons which can be hydroborated in accordance with this invention are included those optically active hydrocarbons disclosed in U.S. Pat. No. 3,078,313, Brown. Among the preferred optically active olefinic hydrocarbons which contain from 6 to 20 carbon atoms and can be utilized in forming the di or tri organo boron hydrides are included:

α-patchoulene
cedrene;
limonene;
carvomenthene;
3-menthene;
camphene;
teripinolene;
β-pinene;
γ-fenchene;
γ-terpinene;
$\Delta^4$-carene;
$\Delta^5$-carene; and
$\Delta^5$-androstene.

Particularly preferred among the organo boron hydrides is (+)-di-3-pinanylborane or its optical isomer.

When the compound of formula VI is reacted with (+)-di-3-pinanylborane, the compound of the formula:

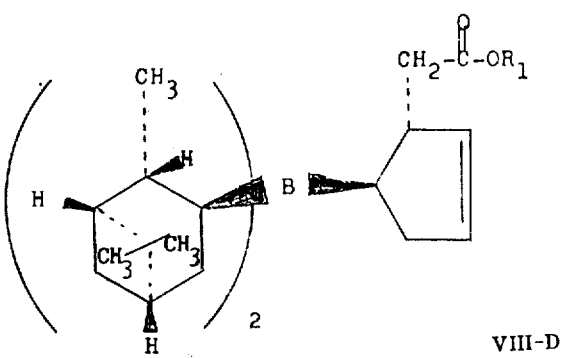

VIII-D wherein $R_1$ is as above;
is formed. On the other hand, when the compound of formula VI is reacted with (−)-di-3-pinanyl-borane, a compound of the formula:

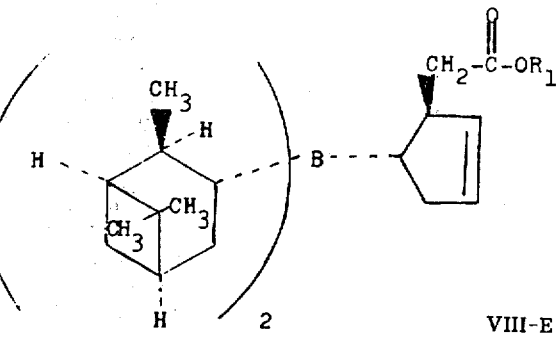

VIII-E wherein $R_1$ is as above;
is prepared.

The compound of formula VIII-A or formula VIII-B is formed by first reacting the compound of formula VI with an optically active organo boronhydride. Whether the compound of formula VIII-A or formula VIII-B forms will depend upon the choice of optically active antipodes of the optically active boron hydride reacted with the compound of formula VI. This reaction is carried out in an inert organic solvent. Any conventional inert organic solvent can be utilized to carry out this reaction. Among the preferred inert solvents for use in this reaction are the ether solvents such as those mentioned hereinbefore. The preferred ether solvent for use in this reaction is tetrahydrofuran. This reaction is carried out at a temperature of from −100°C. to 30°C. Generally, it is preferred to utilize a temperature of from −90°C. to −20°C. The compound of formula VIII-A or its optically active antipode, the compound of formula VIII-B, is converted to the compound of formula VII or its optically active antipode, i.e., the compound of formula VII-A, by treating the compound of formula VIII-A or formula VIII-B with an alkali metal hydroperoxide or perorganic acid. This reaction is carried out in an inert organic solvent or in the reaction medium where the compound of formulae VIII-A or VIII-B is formed. Any conventional inert organic solvent can be utilized. The preferred inert organic solvents are either solvents such as mentioned hereinbefore with tetrahydrofuran being preferred. Temperatures of from −10° to +20°C. can be utilized, with temperatures of from −5° to +5°C. being preferred.

Where a per-organic acid is used, any conventional per-organic acid can be utilized. Among the per-organic acids are included per-lower alkanoic acids such as per-acetic acid, and per-aroic acids such as perbenzoic or meta-chloro per-benzoic acid. On the other hand, an alkai metal hydroperoxide can be added to the reaction medium. If desired, the alkali metal hydroperoxide can be generated in the reaction medium by adding hydrogen peroxide and an alkali metal hydroxide to the reaction medium in which the compound of formulae VIII-A or VIII-B was formed. This reaction medium can be then allowed to reach a temperature of from −10°C. to 20°C. to form the compound of formula VII or a compound of the formula VII-A.

In accordance with this invention, the optically active antipode of formula VII is carried through the process to produce either the compound of formula I or the compound of formula II while maintaining its optical integrity. Therefore, if the compound of formula I or compound of formula II is desired, the reaction sequence is carried out utilizing the compound of formula VII. On the other hand, if the compound of formula VII-A is carried through the various reaction steps in the process of this invention, either the compound of formula I-A or formula II-A can be produced. This is true since the compound of formula VIII-A is carried through the entire reaction sequence of this invention while maintaining its optical integrity. Therefore, the process of this invention provides a method for producing prostaglandin $F_{2\alpha}$ or 15-epi-prostaglandin $F_{2\alpha}$ in either its optically active forms without the necessity of resolution.

The optical configuration of the compound of formula VII or its optically active antipode can be inverted by lactonization to a compound of the formula:

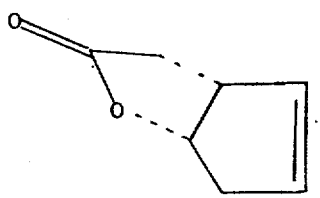

IX or its optically active antipode via an intermediate of the formula:

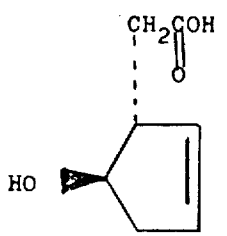

X or its optically active antipode. Also, the optical configuration of the compound of formula VII or its optically active antipode can be inverted to a compound of formula IX above via an intermediate of the formula:

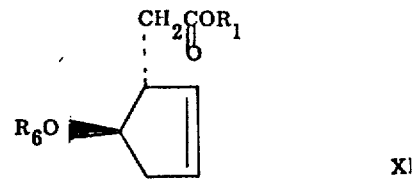

XI wherein $R_1$ is as above; and $-OR_6$ forms a leaving group;
or its optically active antipode.

In converting the compound of formula VII or its optically active antipode to a compound of formula IX or its optically active antipode via the intermediate of the formula X or its optically active antipode, the compound of formula VII or its optically active antipode is first hydrolyzed to produce a compound of formula X or its optically active antipode. Any conventional method of ester hydrolysis can be utilized to convert the compound of formula VII or its optically active antipode to the compound of formula X or its optically active antipode. This hydrolysis is generally accomplished by treatment with an inert organic base such as an alkali metal hydroxide. In carrying out this reaction, an aqueous medium is preferably utilized. This reaction is carried out utilizing any of the conditions conventional in basic hydrolysis. In carrying out this reaction, temperature and pressure are not critical and this reaction can be carried out at room temperature.

The compound of formula X or its optically active antipode is converted to the compound of formula IX or its optically active antipode by lactonization through treatment with an acid halide of an organic sulfonic acid in the presence of an organic amine base. Any conventional halide of an organic sulfonic acid can be utilized. Among the preferred organic sulfonic acids are the lower alkyl sulfonic acids such as methyl sulfonic acid; aryl sulfonic acids and aralkyl sulfonic acids. Among the preferred aryl and aralkyl sulfonic acids suitable for use in this invention are those where the aryl group is phenyl or phenyl substituted with either a nitro, lower alkyl or halo substituent. Among these aryl sulfonic acids and aralkyl sulfonic acids are included benzene sulfonic acid, toluene sulfonic acid, p-nitrobenzene sulfonic acid, chlorobenzene sulfonic acid, and benzyl sulfonic acid. The organic amine base serves as a solvent for this reaction. Any conventional organic amine base such as the lower alkyl amines and heterocyclic amines can be utilized in this reaction. Among the preferred organic amine bases are included triethyl amine, trimethyl amine and pyridine. In carrying out this reaction, temperature and pressure are not critical and this reaction can be carried out at room temperature and atmospheric pressure. On the other hand, elevated or reduced temperatures can be utilized. Generally, it is preferred to carry out this reaction at a temperature of from −10° to 40°C. While the hydroxy group and the carboxymethyl groups are on the opposite sides of the plane of the cylcopentyl ring moiety of the compound of formula X or its optically active antipode, lactonization by this procedure causes the formation of the lactone ring on the same side of the cyclopentyl ring moiety as the carboxymethyl substituent. Hence, this procedure causes inversion through lactonization.

The compound of formula VII or its optically active antipode can be converted to the compound of formula IX or its optically active antipode via an intermediate of the formula XI or its optically active antipode. The compound of formula VII or its optically active antipode is converted to the compound of formula XI or its optically active antipode by means of converting the free hydroxy group to a leaving group. Any conventional method of forming a leaving group can be utilized. Among the preferred leaving groups which form $R_6O$ are the leaving groups formed from organic sulfonic acids such as organic sulfonyl groups. Among the preferred organic sulfonyl groups are included lower alkyl sulfonyl, aryl sulfonyl and aryl alkyl sulfonyl. The preferred lower alkyl sulfonyl is methyl sulfonyl. The preferred aryl sulfonyl and aralkyl sulfonyl groups are those where the aryl substituent is phenyl or phenyl substituted with a lower alkyl, halo or nitro substituent. These aryl sulfonyl or aralkyl sulfonyl groups include toluene sulfonyl, benzene sulfonyl, p-nitrobenzene sulfonyl, p-chlorobenzene sulfonyl and benzyl sulfonyl. The leaving group is prepared in accordance with a preferred embodiment by reacting the compound of formula VII or its optically active antipode with a reactive derivative of an organic sulfonic acid such as an organic sulfonic acid halide or an organic sulfonic acid anhydride in the presence of an organic amine base. Any of the conventional organic amine bases hereinbefore mentioned can be utilized in carrying out this reaction. Generally, this reaction is carried out at a temperature of from about −10° to 40°C.

The compound of formula XI or its optically active antipode is converted to the compound of formula IX or its optically active antipode by treating the compound of formula XI or its optically active antipode with aqueous alkali metal hydroxide. Any of the conditions conventional in ester hydrolysis can be utilized to carry out this reaction. Generally, it is preferred to carry out this reaction by treating the compound of formula XI or its optically active antipode with an alkali metal base such as sodium hydroxide in an aqueous medium. Generally, for convenience, it is preferred to use from 0.1 to 1.5 molar equivalents of base per molar equivalent of the compound of formula XI or its optically active antipode. However, a molar excess of base can be utilized to carry out this reaction. If desired, an inert organic solvent can be present in the reaction medium. Any conventional inert organic solvent can be present in the reaction medium. Among the preferred solvents are the ether solvents such as tetrahydrofuran, diethyl ether, dioxane, etc. Beside lactonization, this basis hydrolysis causes inversion of the stereo configuration. This can be seen by the fact that while the leaving group and the carboxymethyl group are on opposite sides of the plane formed by the cyclopentyl ring moiety in the compound of formula XI or its optically active antipode, treatment with base causes the lactone ring to form on the same side of the plane of the cyclopentyl moiety as the carboxymethyl substituent. In carrying out this lactonization, temperature and pressure are not critical and this reaction can be carried out at room temperature and atmospheric pressure. However, higher or lower temperatures can be utilized, i.e., temperatures of from −10°C. to 60°C.

If excess base is utilized in the lactonization of the compound of formula XI above or its optically active antipode, the yield of the compound of formula IX or its optically active antipode will be reduced by the formation of an alkali metal salt of a compound of the formula:

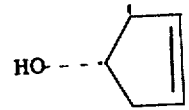

XIII or its optically active antipode as a side product. The alkali metal salt of a compound of formula XIII or its optically active antipode can be converted to the compound of formula IX or its optically active antipode by neutralizing, to a pH of from 4-7, the reaction medium through the addition of an acid such as a strong inorganic or organic acid such as sulfuric acid or hydrohalic acid. Among the preferred acids are aqueous hydrochloric acid and aqueous sulfuric acid. The use of an acid to neutralize the reaction mixture increases the yield of the compound of formula IX or its optically active antipode produced by this procedure.

The compound of formula IX or its optically active antipode can be converted to the compound of formula III or its optically active antipode via the intermediate of the formula:

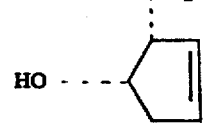

XII and its optically active antipode.

The compound of formula IX or its optically active antipode is converted to the compound of formula XII or its optically active antipode by treating the compound of formula IX or its optically active antipode with an aluminum hydride reducing agent. In utilizing an aluminum hydride reducing agent, any conventional aluminum hydride reducing agent can be utilized. Among the aluminum hydrides that can be utilized are included lithium aluminum hydride, sodium aluminum hydride, diisobutylaluminum hydride, diisopropylaluminum hydride and sodium bis(2-methoxyethoxy)-aluminum hydride. This reduction is carried out in an inert organic solvent medium. Any conventional inert organic solvent can be utilized in carrying out this reaction. Among the preferred inert organic solvents are included tetrahydrofuran, dioxane, diethyl ether, hexane, toluene, benzene or xylene. This reaction can be carried out at room temperature, i.e., 25° C. and atmospheric pressure. On the other hand, reduced or elevated temperatures are preferred, i.e., from −30° to about 80° C., with temperatures of from 10° to 40° C. being especially preferred.

The compound of formula XII or its optically active antipode is converted to the compound of formula III or its optically active antipode by treating the compound of formula XII or its optically active antipode with an organic peracid. Any conventional organic peracid can be utilized in this reaction. Among the conventional organic peracids are included peracetic acid, perbenzoic acid, meta-chloroperbenzoic acid and mono-perphthalic acid. This reaction is usually carried out in an inert organic solvent. Any conventional inert organic solvent can be utilized. Among the preferred inert organic solvents are aliphatic hydrocarbons, aromatic hydrocarbons and halogenated hydrocarbons such as hexane, benzene, methylene chloride, and chloroform or lower alkanoic acids such as acetic acid. Generally, this reaction is carried out at a temperature of from about $-20°$ to $30°C$.

The compound of formula XII or its optically active antipode before its conversion to the compound of formula III or its optically active antipode can be esterified. By esterifying the compound of formula XII or its optically active antipode, with one equivalent of an esterifying agent, only the hydroxy group on the hydroxyethylene radical is esterified. This esterifying can be carried out by conventional means such as be treatment with an active derivative of an organic acid such as lower alkanoic acid chloride or anhydride. The compound of formula XII or its optically active antipode with the hydroxy group of the hydroxyethylene substituent esterified and the free hydroxy moiety attached to the cyclopentene ring can be converted to the compound of formula III or its optically active antipode by treatment with an organic peracid as described hereinbefore. The compound of formula III or its optically active antipode having the hydroxy group of the hydroxyethylene group esterified can be hydrolyzed to the free hydroxyethylene group by conventional basic hydrolysis as described above. The use of the esterified hydroxyethylene group in the compound of formula XII or its optically active antipode provides a compound of the formula III or its optically active antipode.

By epoxidizing the compound of formula XII or its optically active antipode with an organic peracid, the epoxy ring is formed exclusively on the same side of the plane of the cyclopentane moiety as both the hydroxymethylne and hydroxy substituents.

In accordance with another embodiment of this invention, this process provides a new and improved procedure for producing the compound of formula III as a racemate. The racemate of formula III is a known intermediate in the production of racemic prostaglandin $F_{2\alpha}$, Fried, *Journal of American Chemical Society*, 94, 4343 (1972). In this procedure, the compound of formula VI is first converted to a racemate of formula VII by forming a borane complex of the compound of formula VII which has the formula:

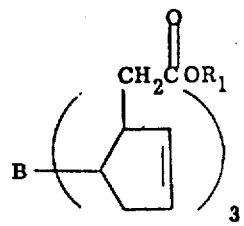

wherein $R_1$ is as above; and the boron is attached to the cyclopentene moiety on the opposite side of the plane as the methylene carboxy ester.

This complex is formed by reacting the compound of formula VI with borane under the same conditions described in forming the compound of formula VIII-A or formula VIII-B from the compound of formula VI. This borane complex is converted to the racemate of formula VII by treatment with an alkali metal hydroperoxide or an organic peracid in the same manner as described in connection with the formation of the optically active compounds of formula VII. The racemate of formula VII can be converted to the racemic lactone of formula IX via the racemic form of the intermediate of formula X or via the racemic form of the intermediate of formula XI by the procedure described hereinbefore. This racemic lactone can be converted to the racemic form of the compound of formula III via the racemic form of the intermediate of formula XII by the procedure described hereinbefore.

The compound of formula IX or its optically active antipode can be converted to the compound of formula IV or its optically active antipode via the following intermediates:

and

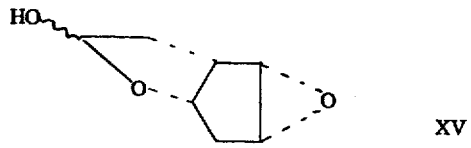

or their optically active antipodes.

The compound of formula IX or its optical active antipode is converted to the compound of formula XIV or its optically active antipode by treating the compound of formula IX with an organic peracid, preferably peracetic acid. The same conditions described in connection with the conversion of a compound of formula XII to a compound of the formula III can be utilized in converting the compound of formula IX or its optical antipode to the compound of formula XIV, or its optical antipode. In this conversion, the epoxide bridge is formed on the same side of the cyclopentane nucleus as the lactone ring.

The compound of formula XIV or its optically active antipode is converted to the compound of formula XV or its optically active antipode by treating the compound of formula XIV with diisobutyl aluminum hydride. This reaction is carried out at a temperature of from $-90°C$. to $-50°C$. with temperatures of from $-85°$ to $-60°C$. being preferred. In carrying out this reaction, any conventional inert organic solvent can be utilized. Among the preferred inert organic solvents are hydrocarbon solvents such as the aromatic and aliphatic hydrocarbons. Among the preferred solvents are included toluene, benzene, xylene, etc.

The compound of formula XV or its optically active antipode is converted to the compound of formula IV or its optically active antipode by conventional etherification techniques. In accordance with the process of this invention, it has been unexpectedly discovered that when the compound of formula XV or its optically active antipode is etherified, the ether group in the compound of formula IV or its optically active antipode is attached to the plane of the molecule in an opposite direction from the epoxy substituent. Therefore, if the epoxy group is in the alpha-orientation, the ether group is in the beta-orientation. On the other hand, if the epoxy group is in the beta-orientation, the ether group is in the alpha-orientation. Therefore, if one etherifies the compound of formula XV, one would obtain the compound of formula IV. On the other hand, if one etherifies the optical antipode of the compound of formula XV which has the formula:

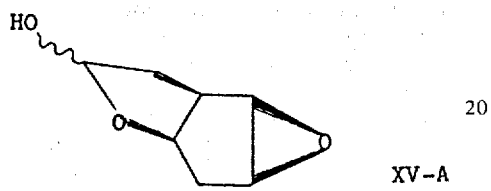

XV-A one obtains the optical antipode of a compound of formula IV having the formula:

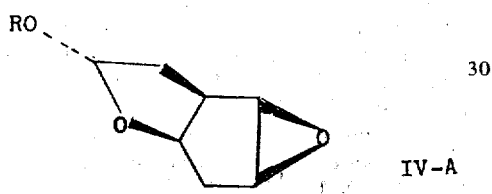

IV-A wherein R is as above.

As stated before, the ether group can be formed by any conventional method of etherifying a hydroxy group. The preferred ethers are the lower alkyl ethers. Among the preferred methods for forming ethers are by treating the compound of formula XV or its optically active antipode with a lower alkanol in the presence of an acid catalyst. Any conventional acid catalyst can be utilized in carrying out this reaction. Among the preferred acid catalysts are acidic cation exchange resins such as polystyrene sulfonic acid resin; inorganic acids such as sulfuric acid, the Lewis acids, such as boron trifluoride, aluminum trichloride, etc. and organic acids such as p-toluenesulfonic acid. Generally, the lower alkanol can serve as the solvent medium. In carrying out this reaction, temperatures of from $-40°C$. to $10°C$. are utilized. The preferred catalyst for use in this reaction is boron trifluoride.

The compound of formula IV or its optically active antipode can be converted to the compound of formulae I or I-A as well as the compound of formula II or II-A via the following intermediates:

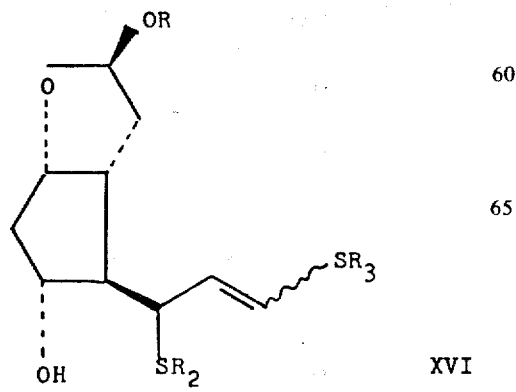

XVI wherein $R_2$ and $R_3$ are lower alkyl; and R is as above;

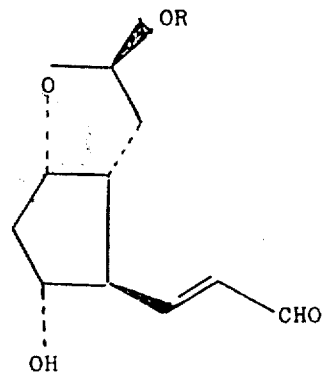

XVII;

wherein R is as above;

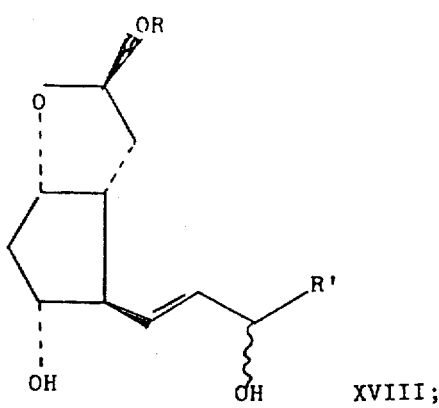

XVIII;

wherein R and R' are as above

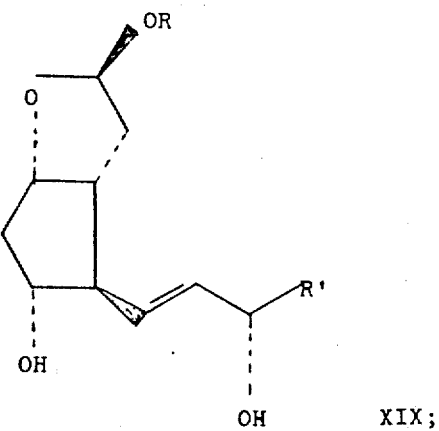

XIX;

wherein R and R' are as above;

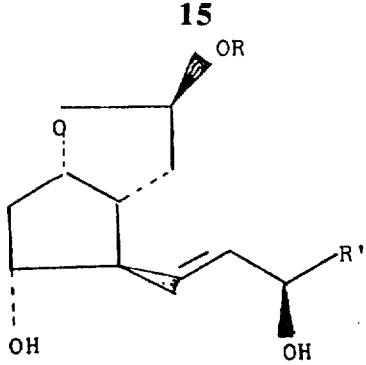

wherein R and R' are as above;

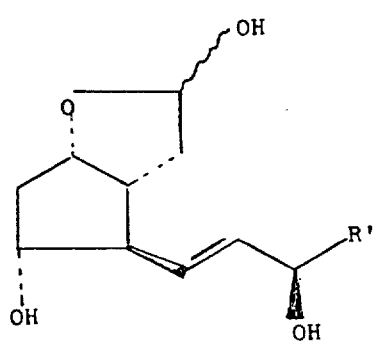

wherein R' is as above;
and

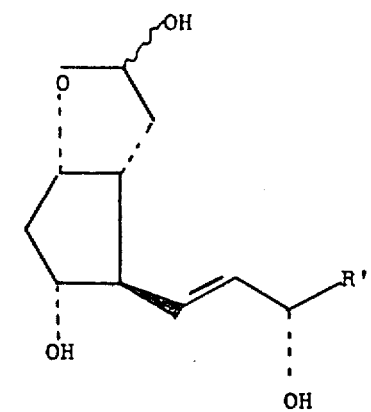

wherein R' is as above.

Where it is desired to prepare the compound of formulae I-A or II-A, the optically active antipode of the compound of formula IV is converted via the optically active antipodes of the compounds of formulae XVI, XVII, XVIII, XIX, XX, XXI and XXII to the compound of formulae I-A or II-A.

The compound of formula IV or its optically active antipode is converted to the compound of formula XVI or its optically active antipode by reacting the compounds of the formula IV or its optically active antipode with a compound of the formula:

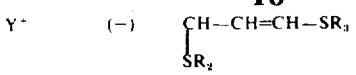

wherein Y is an alkali metal or MgX';
X' is chlorine, bromine or iodine; and
$R_2$ and $R_3$ are as above.

The compound of formula IV or its optically active antipode is reacted with the compound of formula XXV utilizing conditions conventional in Grignard reactions to produce the compound of formula XVI or its optically active antipode. This reaction is carried out in an inert organic solvent medium. Among the preferred solvents are diethyl ether and tetrahydrofuran. In carrying out this reaction, temperature and pressure are not critical and this reaction can be carried out at room temperature and atmospheric pressure. Generally, it is preferred to carry out this reaction at a temperature of from $-90°$ to $-50°C$.

The compound of formula XVI or its optically active antipode is converted to the compound of formula XVII or its optically active antipode by treating the compound of formula XVI or its optically active antipode with a mercuric salt such as mercuric chloride in the presence of a base such as calcium carbonate and water. This reaction can take place in the presence of an inert organic solvent such as acetonitrile. In carrying out this reaction, temperature and pressure are not critical and this reaction can be carried out at room temperature. If desired, temperatures as high as 60° or as low as 10° C. can be utilized.

The compound of formula XVIII or its optically active antipode is prepared by treating the compound of formula XVII or its optically active antipode with a compound of the formula:

$$Y-CH_2-CH_2-CH_2-CH_2-CH_3 \quad XXV-A$$

wherein Y is as above.

This reaction is carried out under the same conditions described in connection with the reaction of the compound of formula IV with a compound of the formula XXV to produce a compound of the formula XVI. The compound of the formula XVIII or its optically active antipode can be separated into its two isomers, i.e., the compound of formula XIX or its optically active antipode and the compound of formula XX or its optically active antipode by any conventional method of separation such as chromatography.

The compound of formula XVIII or its optically active antipode contains approximately equal parts by weight of a mixture of the compound of formula XIX and XX or their optically active antipodes. On the other hand, if one wishes to produce the compound of formula XIX or its optically active antipode in higher yields than that obtained by the foregoing procedure, the compound of formula XVII or its optically active antipode is converted to the compound of formula XIX via the following intermediates:

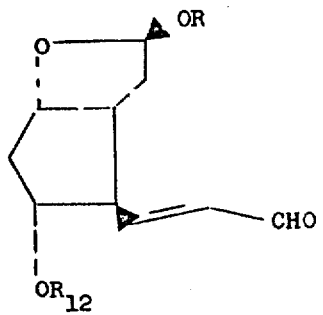

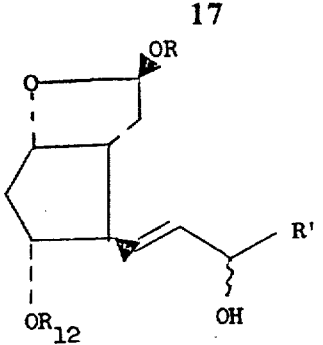

XXIV

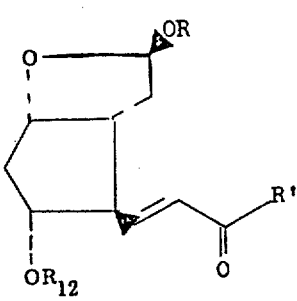

XXVI

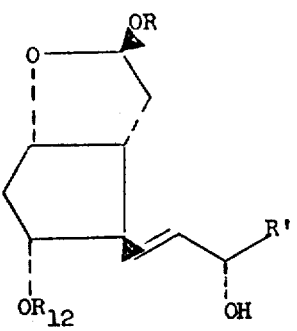

XXVII and

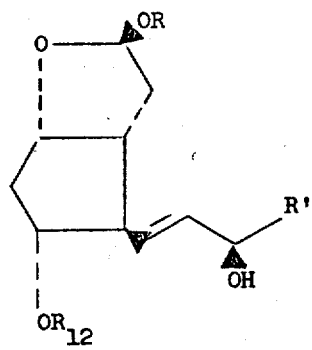

XXVIII wherein R and R' are as above and —OR$_{12}$ forms hydroxy or hydroxy protected by ester groups convertible to hydroxy by hydrolysis
and their optically active antipodes.

The free hydroxy group in the compound of formula XVII or its optically active antipode can be protected, if desired. Any conventional method of esterifying a hydroxy group can be utilized. Among the preferred esters are the aroic esters and as benzoyl a p-phenyl benzoyl and the aryl carbamate esters such as phenyl carbamate or p-phenylphenylcarbamate. The compound of formula XXIII or its optically active antipode is converted to the compound of formula XXIV or its optically active antipode by reaction with a compound of formula XXV-A in the same manner as described hereinbefore.

The compound of formula XXIV or its optically active antipode can be converted to the compound of formula XXVI by oxidizing with manganese dioxide, dichloro-5,6-dicyanobenzoquinone, or a chromate oxidizing agent such as chromium trioxide. Where chromium trioxide is utilized, the free hydroxy group should be protected by an ester. On the other hand, where manganese dioxide or 2,3-dichloro-5,6-dicyanobenzoquinone is utilized, OR$_{12}$ in the compound of formula XXIV or its optically active antipode can be hydroxy or can form an ester group. The compound of formula XXVI or its optically active antipode is reduced to form the compound of formula XXVII or its optically active antipode. This reduction is carried out utilizing an alkali metal triloweralkyl borohydride reducing agent. It has been found that when the compound of formula XXVI or its optically active antipode is reduced with an alkali metal trialkylborohydride reducing agent, the compound of formula XXVII or its optically active antipode is produced with only a small amount of the compound of formula XXVIII or its optically active antipode. Therefore, if it is desired to produce the compound of formulae I or I-A rather than the compound of formulae II or II-A, it is preferable to prepare the intermediates of the formulae XXIV, XXVI and XXVII or their optically active antipodes in the conversion of a compound of the formula XVII or its optically active antipode to the compound of the formula XIX or its optically active antipode.

The reduction of the compound of the formula XXVI or its optically active antipode with an alkali metal triloweralkyl borohydride reducing agent is carried out utilizing the conditions conventional in reduction with an alkali metal trialkyl borohydride reducing agent except that temperatures of from −110° to −50° C. are utilized. The mixture thus produced contains predominantly the compound of formula XXVII or its optically active antipode and a minor amount of the compound of formula XXVIII or its optically active antipode. These compounds can be separated by any conventional method of separation such as chromatography. Any conventional method of chromatography can be used to make this separation. The compounds of formulae XXVII or XXVIII where —OR$_{12}$ forms an ester protecting group or their optically active antipodes can be respectively converted to the compound of formulae XIX or XX or their optically active antipodes by ester hydrolysis. Any conventional method of ester hydrolysis such as treatment with an alkali metal hydroxide in an aqueous medium can be utilized to carry out this conversion.

The compound of formula XIX is converted into the compound of formula I via the intermediate of the compound of formula XXII. On the other hand, if the optical antipode of the compound of formula XIX is treated in the same manner, the compound of formula I-A is formed via the optical antipode of the compound of formula XXII. On the other hand, the compound of formula XX is converted to the compound of formula II via the intermediate of the formula XXI. If the optical antipode of the compound of formula XX is utilized, the compound of formula II-A is produced via the optical antipode of the intermediate of the compound of formula XXI.

The compound of the formula XIX or its optically active antipode is converted to the compound of formula XXII or its optically active antipode and the compound of formula XX or its optically active antipode is converted to the compound of formula XXI or its optically active antipode by means of ether hydrolysis. Any conventional method of ether hydrolysis can be utilized to carry out this reaction. Among the preferred methods of ether hydrolysis is by treating the compounds of formulae XIX or XX or their optically active antipode with a strong inorganic acid such as hydrochloric or sulfuric acid in an aqueous medium.

The compound of formula XXII or its optically active antipode is converted to the compound of formula I and the compound of formula XXI is converted to the compound of formula II by reaction with an alkali metal salt of the compound of the formula:

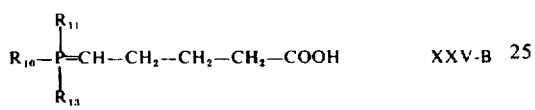

XXV-B wherein $R_{10}$, $R_{11}$ and $R_{13}$ are aryl or lower alkyl.
This reaction is carried out under conditions conventional for a Wittig type synthesis. Any of the conditions conventionally used in Wittig type synthesis can be utilized in carrying out this reaction.

In accordance with a further embodiment of this invention, the compound of formula III or its optically active antipode is converted to the compound of formulae I or II or their optically active antipodes via the following intermediates:

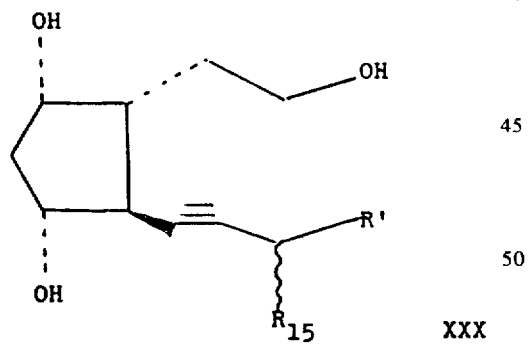

XXX wherein $R_{15}$ is ~OR, ◂OR or ----OR; and —OR is as above;

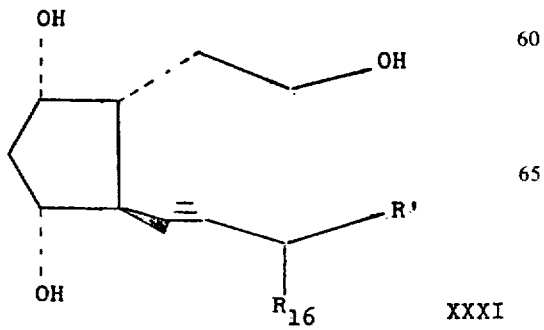

XXXI wherein R' is as above; and $R_{16}$ is ~OH, ◂OH or ----OH;

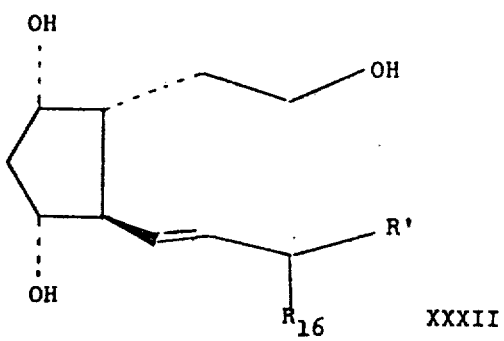

XXXII wherein R' and $R_{16}$ are as above;

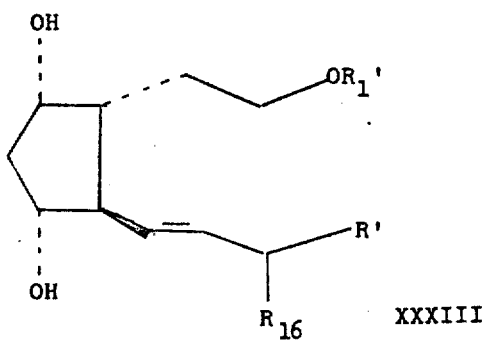

XXXIII wherein R' and $R_{16}$ are as above; and —$OR_1$' forms an ether protecting group convertible to hydroxy by hydrolysis;

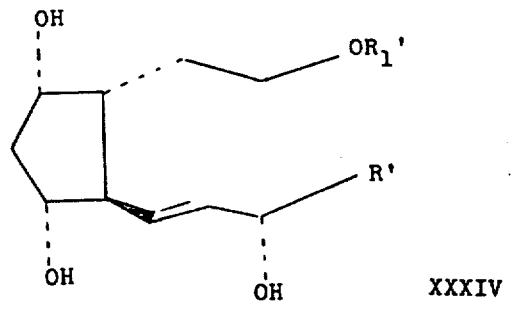

XXXIV wherein $R_1$' and R' are as above;

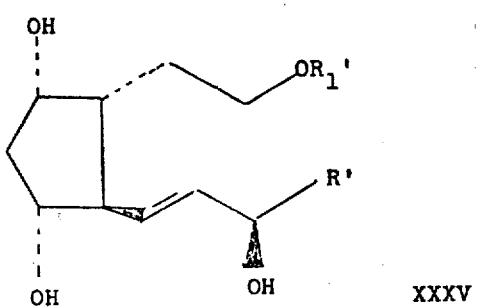

XXXV wherein $R_1'$ and $R'$ are as above;
or their optically active antipodes.

In converting the compound of formula III or its optically active antipode to the compound of formula XXX or its optically active antipode, the compound of formula III is reacted with a compound of the formula:

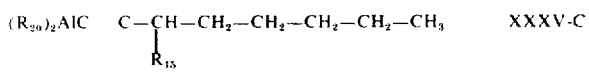

$$(R_{20})_2 AlC \quad C-\underset{R_{15}}{CH}-CH_2-CH_2-CH_2-CH_2-CH_3 \qquad \text{XXXV-C}$$

wherein $R_{15}$ is as above; and $R_{20}$ is lower alkyl.

This reaction is carried out utilizing conditions conventional in carrying out Grignard reactions. In carrying out this reaction, temperatures of from 50 to 70°C. are preferred. Furthermore, the preferred inert organic solvents are aromatic hydrocarbons such as benzene and toluene.

Where it is desired to produce a compound of formulae I or II-A, $R_{15}$ in the compound of formula XXXV-C is ---OR. When it is desired to produce a compound of formulae I-A or II, $R_{15}$ in the compound of formula XXXV-C is ◄OR. On the other hand, where it is desired to produce a compound of the formulae XXX, XXXI, XXXII and XXXIII as a mixture of isomers, the compound of formula XXXV-C is utilized where $R_{15}$ is ~OR.

The compound of formula XXX or its optically active antipode is converted to the compound of formula XXI or its optically active antipode by ether hydrolysis. Any conventional method of ether hydrolysis can be utilized for this conversion. Among the preferred methods of hydrolysis is by treating the compound of formula XXX or its optically active antipode with a strong acid such as sulfuric acid, trifluoroacetic acid or hydrochloric acid at a temperature of from −10° to +10°C. The compound of formula XXXI or its optically active antipode can be converted to the compound of formula XXXII or its optically active antipode by reduction with alkali metal aluminum hydride. Any conventional method of reducing a triple bond to a double bond with an alkali metal aluminum hydride reducing agent can be utilized in carrying out this reaction. Generally, it is preferred to carry out this reaction at a temperature of from about 40 to 80°C. in the presence of an ether solvent such as tetrahydrofuran. The compound of formula XXXII or its optically active antipode is converted to the compound of formula XXXIII or its optically active antipode by etherification with one equivalent of an etherifying agent. Any conventional method of etherification can be utilized to convert the free terminal hydroxy group to an ether protecting group. IN the compound of formula XXXII or its optically active antipode, the terminal alkyl hydroxy group is far more reactive than the other hydroxy groups. Therefore, the compound of formula XXXII or its optically active antipode can be selectively etherified by conventional procedures procedures to form the compound of formula XXXIII or its optically active antipode. Among the conventional procedures for etherification which can be utilized are included reacting the compound of formula XXXII or its optically active antipode with a lower alkyl halide or an aralkyl halide such as benzyl halide, or triphenylmethyl halide in the presence of an organic amine base such as pyridine.

Where $R_{16}$ is ~OH in the compound of formula XXXIII or its optically active antipode, this compound can be separated into its two epimeric isomeric forms, i.e., the compound of formula XXXIV or its optically active antipode and the compound of formula XXV or its optically active antipode. Any conventional method of separation can be utilized. Among the preferred methods of separation is chromatography.

On the other hand, where $R_{16}$ is ~OH in the compound of formula XXXIII or its optically active antipode, and one wants to obtain a mixture containing predominantly the isomer where $R_{16}$ is ---OH, the compound of formula XXXIII where $R_{16}$ is ~OH or its optically active atnipode is first oxidized to a compound of the formula:

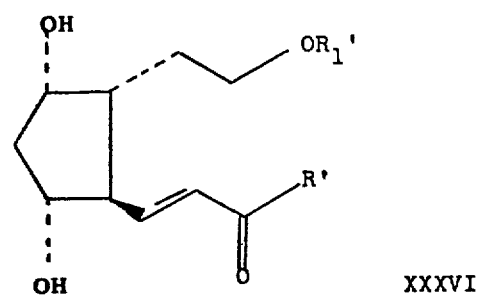

XXXVI wherein $R_1'$ and $R'$ are as above;
or its optically active antipode. This oxidation is carried out with manganese dioxide or 2,3-chloro-5,6-dicyanobenzoquinone as an oxidizing agent. Any of the conditions conventional in utilizing these oxidizing agents can be utilized in carrying out this reaction. The compound of formula XXXVI or its optically active antipode is then reduced to produce a mixture containing predominantly the compound of formula XXXIV or its optically active antipode and a minor amount of the compound of formula XXXV or its optically active antipode. This mixture can be separated into the individual isomers by conventional means such as chromatography. The reduction whereby the compound of formula XXXVI or its optically active antipode is converted to a mixture containing predominantly the compound of formula XXXIV or its optically active antipode is carried out by utilizing alkali metal triloweralkylborohydride. Any of the conditions conventional in utilizing these reducing agents can be utilized in carrying out this reduction except that this reaction is carried out at a temperature of from −110°C. to −50°C.

Where $R_{16}$ in the compound of formula XXXII or its optically active antipode is ◄OH or ---OH, this compound can be converted to a compound of the formula:

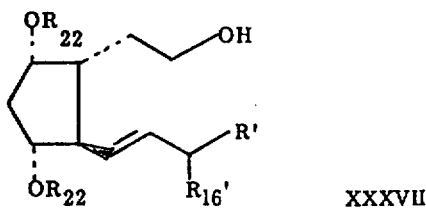

XXXVII wherein —$OR_{22}$ forms an ester protecting group convertible to hydroxy by hydrolysis; and $R_{16}'$ is ----$OR_{22}$ or ◄$OR_{22}$; and R' is as above; or its optically active antipode via an intermediate of the formula:

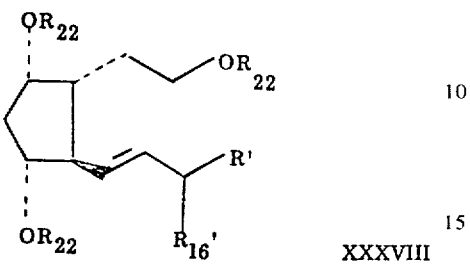

XXXVIII wherein R', $R_{16}'$ and $R_{22}$ are as above. The compound of formula XXXVIII or its optically active antipode is formed by treating the compound of formula XXXII or its optically active antipode with an esterifying agent. Any compound which will esterify an alcohol can be used for this purpose. Among the preferred agents for this purpose are reactive derivatives of an organic acid such as a lower alkanoic acid anhydride or halide. Any of the conditions conventional in esterifying alcohols can be utilized in this reaction. The compound of formula XXXVII or its optically active antipode is formed by hydrolyzing the compound of formula XXXVIII or its optically active antipode with an alkali metal hydroxide in an aqueous medium. In carrying out this hydrolysis only one mole of alkali metal hydroxide should be present per mole of the compound of formula XXXVIII or its optically active enantiomer to prevent hydrolysis of the ester groups attached directly to the cyclopentane nucleus and the ester group attached to a secondary carbon atom on the side chain.

On the other hand, the compound of formulae XXXIV and XXXV or their optically active antipodes can be converted to a compound of formulae XXXVII via an intermediate of the formula:

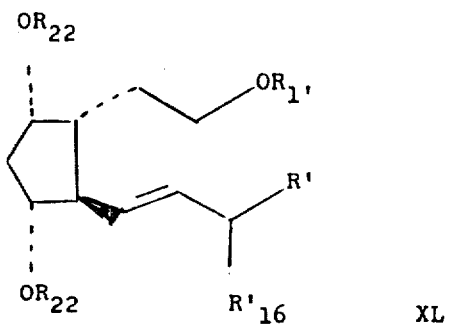

XL wherein R', $R'_{16}$, $R_1'$ and $R_{22}$ are as above; or its optically active antipode.

The compound of formulae XXXIV and XXXV or their optically active antipodes are converted to the compound of formula XL or its optically active antipode by esterification in the manner described hereinbefore. The compound of formula XL or its optically active antipode is converted to the compound of formula XXXVII or its optically active antipode by ether hydrolysis. Any conventional method of ether hydrolysis such as treatment with a strong inorganic acid can be utilized.

The compound of formula XXXVII or its optical active antipode is converted to the compound of formulae I or II or their optically active antipodes via the following intermediates:

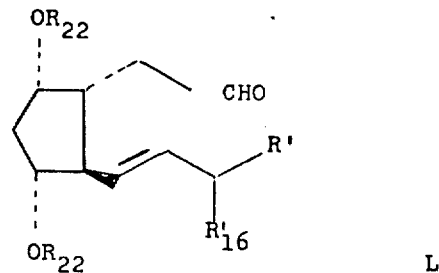

L wherein R', $R_{22}$ and $R'_{16}$ are as above;

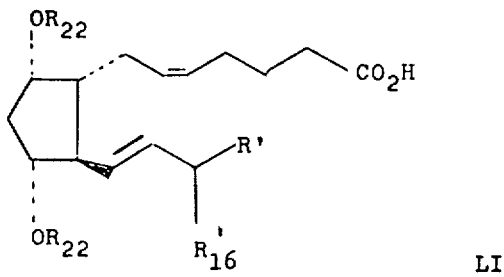

LI wherein $R_{22}$, $R_{16}'$ and $R_{22}$ are as above; or their optically active antipodes.

The compound of formula XXXVII or its optically active antipode is converted to the compound of formula L or its optically active antipode by oxidizing the free hydroxy group to an aldehyde group. In carrying out this reaction, many of the conventional oxidizing agents for converting alcohols to aldehydes can be utilized. Among the preferred oxidizing agents for use in this process are the chromate oxidizing agents such as chromium trioxide in pyridine and dimethylsulfide in halogenated hydrocarbon solvent in the presence of halogen or a N-halo succinimide followed by the addition of an organic base such as triethylamine. Any of the conditions conventional in these oxidizing agents can be utilized in carrying out this reaction.

The compound of formula L or its optically active antipode is converted to the compound of formula LI or its optically active antipode by reacting the compound of formula L or its optically active antipode via a Wittig reaction with an alkali metal salt of the compound of the formula:

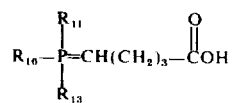

XXV - B wherein $R_{10}$, $R_{11}$ and $R_{13}$ are as above.

The compound of formula XXV-B is reacted with a compound of formula L or its optically active antipode to produce a compound of formula LI or its optically active antipode, utilizing any of the conditions conventional in carrying out Wittig reactions. The compound of formula LI or its optically active antipode can be converted to the compound of formulae I or II or their optically active antipodes by basic hydrolysis. Any conventional method of basic hydrolysis can be utilized to carry out this reaction. Among the preferred methods of basic hydrolysis is to react the compound of formula LI or its optically active antipode with an alkali metal base in an aqueous medium at a temperature of from 10° to 50°C.

The invention will be more fully understood from the specific examples which follow. These examples are intended to be illustrative of the invention, and are not to be construed limitative thereof. The temperature in these examples is in degrees centigrade and the ether utilized is diethyl ether. The term concentrated sulfuric acid denotes a mixture containing 4% by water and 96% by weight sulfuric acid. The term concentrated hydrochloric acid denotes an aqueous solution containing 38% by weight of hydrogen chloride.

EXAMPLE 1

A solution of cyclopentadienylsodium was prepared from 20.5 g. (0.90 g. at.) of sodium metal and 39.6 g. (0.60 mole) of cyclopentadiene at −10° centigrade in 300 ml. of tetrahydrofuran. The solution was filtered through glass wool and added dropwise to a solution of 91.8 g. (0.60 mole) of methyl bromoacetate and 150 ml. of tetrahydrofuran maintained at −78°C. The cold mixture was stirred for 16 hours at −78°C. to generate methyl 2,4-cyclopentadiene-1-acetate.

During this time (+)-di-3-pinanylborane was prepared by adding 600 ml. (0.60 mole) of 1 M borane in tetrahydrofuran to 180.4 g. (1.33 mole) of (−)-alpha-pinene at 0°C. and stirring the mixture for 16 hours at 0°C. The suspension was cooled to −78° centigrade and the cold solution of methyl 2,4-cyclopentadiene-1-acetate was added. The mixture was stirred at −78°C. for 6 hours and at 0 degrees centigrade for 16 hours to produce 2(S)-methoxycarbonylmethyl-3-cyclopenten-1R-yl-bis {(1S,2R,3R,5R)-2,6,6-trimethylbicyclo [3.1.1] heptan-3-yl} borane.

A solution of 60 ml. of 3 N aqueous sodium hydroxide was added to the reaction mixture at 0°C. followed by the dropwise addition of 60 ml. of 30% by weight hydrogen peroxide in water at 0 degrees centigrade. A total of 3 g. of sodium bisulfite was added to the stirred mixture followed by 5 g. of sodium chloride. The mixture was extracted with 3 × 250 ml. of diethyl ether. The ether layers were combined and washed with 100 ml. of water and 100 ml. of saturated brine. The solution was dried over anhydrous magnesium sulfate and evaporated to dryness to yield 201.6 g. of an oil. Distillation at 68°–73°C. (0.09 mm.) yielded 25.8 g. of a mixture of products.

The 25.8 g. of product mixture was dissolved in 600 ml. of diethyl ether and washed with 3 × 250 ml. of 1 M aqueous silver nitrate solution and the ether layer was discarded. The aqueous layers were combined and saturated with excess sodium chloride. The solution was then extracted with 3 × 250 ml. of diethyl ether. The ether layers were washed with 100 ml. of water and 100 ml. of saturated brine. The solution was dried over anhydrous magnesium sulfate and evaporated to dryness. Distillation at 65°–66°C. (0.03 mmHg.) yielded methyl 2R-hydroxy-4-cyclopentene-1R-acetate; b.p. = 80°–81° centigrade (0.1 mmHg.)

EXAMPLE 2

A solution of cyclopentadienylsodium was prepared from 20.5 g. (0.90 g. at) of sodium metal and 39.6 g. (0.60 mole) of cyclopentadiene at −10°C. in 250 ml. of tetrahydrofuran. The solution was filtered through glass wool and added dropwise to a solution of 91.8 g. (0.60 mole) of methyl bromoacetate and 200 ml. of tetrahydrofuran maintained at −78°C. The cold mixture was stirred for 16 hours at −78°C. to form methyl 2,4-cyclopentadiene-1- acetate.

During this time (−)-di-3-pinanylborane was prepared by adding 800 ml. (0.80 mole) of 1 M borane in tetrahydrofuran to 239.8 g. (1.76 mole) of (+)-alpha-pinene at 0°C. and stirring the mixture for 16 hours at 0°C. The suspension was cooled to −78° centigrade and the cold solution of methyl 2,4-cyclopentadiene-1-acetate was added. The mixture was stirred at −78° centigrade for 6 hours and at 0°C. for 16 hours to produce 2R-methoxycarbonylmethyl-3-cyclopenten-1S-yl-bis {(1R,2S,3S,5S)-2,6,6-trimethylbicyclo [3.1.1] heptane-3-yl} borane.

A solution of 60 ml. of 3 N aqueous sodium hydroxide was added to the reaction mixture at 0°C. followed by the dropwise addition of 60 ml. of 30% by weight aqueous hydrogen peroxide at 0°C. A total of 5 g. of sodium bisulfite was added to the mixture followed by 10 g. of sodium chloride. The mixture was extracted with 3 × 250 ml. of diethyl ether. The ether layers were combined and washed with 100 ml. of water and 100 ml. of saturated brine. The solution was dried over anhydrous magnesium sulfate and evaporated to dryness to yield 300 g. of a mixture of products.

The product mixture was dissolved in 500 ml. of diethyl ether and washed with 3 × 250 ml. of 1 M aqueous silver nitrate solution and the ether layer was discarded. The aqueous layers were combined and saturated with excess sodium chloride. The solution was then extracted with 3 × 250 ml. of diethyl ether. The ether layers were washed with 100 ml. of water and 100 ml. of saturated brine. The solution was dried over anhydrous magnesium sulfate and evaporated to dryness. Distillation at 75°–76°C. (0.05 mmHg.) yielded methyl 2S-hydroxy-4-cyclopentene-1S-acetate; b.p. 80°–81° centigrade (0.1 mmHg.).

EXAMPLE 3

A mixture of 2.30 g. of (0.0348 mole) of 85% by weight potassium hydroxide in water, 15 ml. of water, 15 ml. of methanol, and 2.72 g. (0.0174 mole) of methyl 2R-hydroxy-4-cyclopentene-1R-acetate was stirred for 16 hours at room temperature to form a solution containing sodium 2R-hydroxy-4-cyclopentene-1R-acetate.

The solution was diluted with 30 ml. of water and extracted with 3 × 100 ml. of diethyl ether. The combined ether extracts were washed with 50 ml. of water and discarded. The combined water layers were acidified with an excess of 1:1 parts by volume concentrated aqueous hydrochloric acid-ice slurry and extracted with 3 × 50 ml. of diethyl ether. The combined ether layers were washed with 50 ml. of water and discarded.

The combined water layers were evaporated to dryness and the solid residue was triturated with 3 × 150 ml. of hot methylene chloride. The methylene chloride solution was filtered and evaporated to dryness to yield an oil that crystallized on standing.

An analytical sample was obtained by two recrystallizations from diethyl ether-hexane to yield fine needles (m.p. 56°–57°C.) of 2R-hydroxy-4-cyclopentene-1R-acetic acid.

EXAMPLE 4

A mixture of 4.60 g. (0.0696 mole) of 85% by weight potassium hydroxide, in water, 50 ml. of water, 25 ml. of methanol, and 5.44 g. (0.0348 mole) of methyl 2S-hydroxy-4-cyclopentene-1S-acetate was stirred for 16 hours at room temperature to form a solution containing sodium 2S-hydroxy-4-cyclopentene-1S-acetate.

The solution was diluted with 50 ml. of water and extracted with 3 × 100 ml. of diethyl ether. The combined ether extracts were washed with 50 ml. of water and discarded. The combined water layers were acidified with an excess of a 1:1 parts by volume concentrated aqueous hydrochloric acid-ice slurry and extracted with 3 × 100 ml. of diethyl ether. The combined ether layers were washed with 2 × 50 ml. of water and discarded.

The combined water layers were evaporated to dryness and the solid residue was triturated with 3 × 150 ml. of hot methylene chloride. The methylene chloride solution was filtered and evaporated to dryness to yield an oil that crystallized on standing.

An analytical sample was obtained by two recrystallizations from ether-hexane to yield fine needles of 2S-hydroxy-4-cyclopentene-1S-acetic acid; m.p. 56°–57°C.

EXAMPLE 5

To a solution of 0.313 g. (0.0020 mole) of methyl 2R-hydroxy-4-cyclopentene-1R-acetate in 3 ml. of pyridine at 0 degrees centigrade was added dropwise 0.252 g. (0.0022 mole) of methanesulfonyl chloride. The mixture was stirred at 0° centigrade for one hour and poured onto crushed ice. The mixture was diluted with 50 ml. of saturated brine and extracted with 3 × 50 ml. of diethyl ether. The combined ether layers were washed with 50 ml. of 10% by weight sulfuric acid in water, 50 ml. of saturated aqueous sodium bicarbonate solution, and 50 ml. of saturated brine. The solution was dried over anhydrous magnesium sulfate and evaporated to dryness at room temperature to yield the oily methyl 2R-methylsulfonyloxy-4-cyclopentene-1R-acetate.

EXAMPLE 6

To a solution of 0.625 g. (0.0040 mole) of methyl 2S-hydroxy-4-cyclopentene-1S-acetate in 4 ml. of pyridine at 0 degrees centigrade was added dropwise 0.504 g. (0.0044 mole) of methanesulfonyl chloride. The mixture was stirred for 1 hour at 0°C. and was poured onto crushed ice. The mixture was diluted with 50 ml. of saturated brine and extracted with 3 × 50 ml. of diethyl ether. The combined ether layers were washed with 50 ml. of 10% by weight sulfuric acid in water, 50 ml. of saturated aqueous sodium bicarbonate, and 50 ml. of saturated brine. The solution was dried over anhydrous magnesium sulfate and evaporated to dryness at room temperature to yield the oily methyl 2S-methylsulfonyloxy-4-cyclopentene-1S-acetate.

EXAMPLE 7

To a solution of 0.314 g. (0.00134 mole) of methyl 2R-methylsulfonyloxy-4-cyclopentene-1R-acetate, 14 ml. of tetrahydrofuran, and 4 ml. of water at 0°C. was added dropwise 3 ml. (0.0060 mole) of 2 N aqueous sodium hydroxide.

The two-phased solution was vigorously stirred at 0°C. for 1 hour and at room temperature for 18 hours to form a solution containing sodium 2S-hydroxy-4-cyclopentene-1R-acetate.

This solution was diluted with 50 ml. of water and was extracted with 3 × 50 ml. of diethyl ether. The ether extracts were combined, washed with 25 ml. of water and discarded. The water layers were combined, cooled to 0°C., and acidified with excess 6 N aqueous sulfuric acid. The acidic solution was saturated with sodium chloride and extracted with 3 × 50 ml. of methylene chloride. The methylene chloride layers were combined and washed with 50 ml. of saturated aqueous sodium bicarbonate solution. The solution was then dried over anhydrous magnesium sulfate and evaporated to dryness to yield 2S-hydroxy-4-cyclopentene-1R-acetic acid lactone as a white solid (m.p. 45°–46°C).

EXAMPLE 8

To a solution of 0.308 g. (0.00132 mole) of methyl 2S-methylsulfonyloxy-4-cyclopentene-1S-acetate, 14 ml. of tetrahydrofuran, and 4 ml. of water at 0°C. was added dropwise 3 ml. (0.0060 mole) of 2 N sodium hydroxide solution. The two-phased solution was vigorously stirred at 0°C. for 1 hour and at room temperature for 18 hours to form a solution containing sodium 2R-hydroxy-4-cyclopentene-1S-acetate.

The mixture was diluted with 50 ml. of water and was extracted with 3 × 50 ml. of diethyl ether. The ether extracts were combined, washed with 25 ml. of water and discarded. The water layers were combined, cooled to 0°C. and acidified with excess 6 N aqueous sulfuric acid. The acidic solution was saturated with sodium chloride and extracted with 3 × 50 ml. of methylene chloride. The methylene chloride layers were combined and washed with 50 ml. of saturated aqueous sodium bicarbonate solution. The solution was then dried over anhydrous magnesium sulfate and evaporated to dryness to yield 2R-hydroxy-4-cyclopentene-1S-acetic acid lactone as a white solid (m.p. 45°–46°C).

EXAMPLE 9

A mixture of 1.0 ml. of a peracetic acid solution containing 40% by weight peracetic acid, 5% by weight hydrogen peroxide, 39% by weight acetic acid, 15% by weight water and 1% by weight sulfuric acid, 3.0 ml. of acetic acid and 0.40 g. of anhydrous sodium acetate was stirred at 0°C. for 10 minutes. A solution of 0.310 g. (0.0025 mole) of 2S-hydroxy-4-cyclopentene-1R-acetic acid lactone in 1 ml. of acetic acid was added dropwise. The mixture was stirred at 0°C. for 1 hour at room temperature for 16 hours.

The mixture was poured into 50 ml. of water and extracted with 3 × 50 ml. of methylene chloride. The combined methylene chloride layers were washed with 50 ml. of saturated aqueous sodium sulfite solution and 50 ml. of saturated aqueous sodium bicarbonate solution. The aqueous washes were each back-extracted with 25 ml. portions of methylene chloride. The combined methylene chloride layers were dried over anhydrous magnesium sulfate and evaporated to dryness to yield 0.342 g. of a colorless oil.

The oil was triturated with 1 ml. of cold diethyl ether to effect crystallization of the oil. The ether solution was pipetted away from the crystals and evaporated to dryness to yield 0.070 g. of an oil which was discarded.

Recrystallization of the solid from ethyl acetate-heptane at 0°C. yielded a first crop of 1aR,2,2aS,5-,5aS,5bS-hexahydro-4H-oxireno[3,4]cyclopenta[1,2-b]furan-4-one. An analytical sample was secured by an additional recrystallization from ethyl acetate-heptane to yield the furan-4-one as fine colorless needles; m.p. 76°–77°C.

EXAMPLE 10

A mixture of 1.0 ml. of the peracetic acid solution used in Example 9, 3.0 ml. of acetic acid and 0.40 g. of anhydrous sodium acetate was stirred at 0°C. for 10 minutes. A solution of 0.310 g. (0.0025 mole) of 2R-hydroxy-4-cyclopentene-1S-acetic acid lactone in 1 ml. of acetic acid was added dropwise. The mixture was stirred at 0°C. for 1 hour and at room temperature for 16 hours.

The mixture was poured into 50 ml. of water and extracted with 3 × 50 ml. of methylene chloride. The combined methylene chloride layers were washed with 50 ml. of saturated aqueous sodium sulfite solution and 50 ml. of saturated aqueous sodium bicarbonate solution. The aqueous washes were each back-extracted with 25 ml. portions of methylene chloride. The combined methylene chloride layers were dried over anhydrous magnesium sulfate and evaporated to dryness to yield 0.350 g. of a colorless oil.

The oil was triturated with 1 ml. of ether at 0°C. to effect crystallization. The ether solution was pipetted away from the crystals and evaporated to dryness to yield 0.050 g. of an oil that was discarded.

Recrystallization of the solid from ethyl acetate-heptane at 0°C. yielded a first crop of 1aS,2,2aR,5,5aR,5bR-hexahydro-4H-oxireno[3,4]cyclopenta[1,2-b]furan-4-one.

An analytical sample was obtained by an additional recrystallization from ethyl acetate-heptane to yield fine colorless needles of the product; m.p. 76°–77°C.

EXAMPLE 11

A mixture of 0.076 g. (0.0020 mole) of lithium aluminum hydride, 15 ml. of diethyl ether, and 0.248 g. (0.0020 mole) of 2S-hydroxy-4-cyclopentene-1R-acetic acid lactone was stirred at 0°C. for 1 hour. To the solution at 0°C. was added dropwise 0.15 ml. of water followed by 0.12 ml. of an aqueous solution containing 10% by weight sodium hydroxide and the mixture was stirred at 0°C. for 0.5 hour. The solution was then stirred with 0.10 g. of anhydrous magnesium sulfate for 0.5 hour, diluted with 10 ml. of methylene chloride and filtered. The solid residue was triturated with 2 × 10 ml. of methylene chloride and filtered. The combined filtrate was evaporated to dryness to yield 0.265 g. of a colorless viscous oil.

The oil was purified by column chromatography on 5 g. of silica gel (0.05–0.20 mm.). A total of 0.016 g. of impurity was eluted with 10% by volume ethyl acetate in 90% by volume benzene. The 25% by volume ethyl acetate-benzene fractions afforded oily 2R-(2-hydroxyethyl)-3-cyclopenten-1S-ol; b.p. = 83°–84°C. (0.1 mmHg.).

EXAMPLE 12

A mixture of 0.076 g. (0.0020 mole) of lithium aluminum hydride, 15 ml. of diethyl ether, and 0.248 g. (0.0020 mole) of 2R-hydroxy-4-cyclopentene-1S-acetic acid lactone was stirred at 0°C. for 1 hour. To the solution at 0°C. was added dropwise 0.15 ml. of water followed by 0.12 ml. of 10% by weight sodium hydroxide aqueous solution and the mixture was stirred at 0°C. for 0.5 hour. The solution was then stirred with 0.10 g. of anhydrous magnesium sulfate for 0.5 hour, diluted with 10 ml. of methylene chloride and filtered. The solid residue was triturated with 2 × 10 ml. of methylene chloride and filtered. The combined filtrate was evaporated to dryness to yield 0.270 g. of a colorless viscous oil.

The oil was purified by column chromatography on 5 g. of silica gel (0.05–0.20 mm.). A total of 0.016 g. of impurity was eluted with 10% by volume ethyl acetate and 90% by volume benzene. The 25% by volume ethylacetate-benzene fractions afforded 2S-(2-hydroxyethyl)-3-cyclopentene-1R-ol, b.p. 83°–84°C. (0.1 mmHg.).

EXAMPLE 13

To a solution of 0.142 g. (0.0010 mole) of 2R-hydroxy-4-cyclopentene-1R-acetic acid and 1 ml. of pyridine at 0 degrees centigrade was added dropwise 0.115 g. (0.0010 mole) of methanesulfonyl chloride in 1 ml. of pyridine and the mixture was stirred for 1 hour at 0°C. and 18 hours at room temperature to form a solution containing 2R-methylsulfonyloxy-4-cyclopentene-1R-acetic acid.

A total of 0.5 g. of ice was added and the mixture was stirred for 4 hours at room temperature. The mixture was poured into 50 ml. of brine and was extracted with 3 × 50 ml. of methylene chloride. The methylene chloride layers were washed with 50 ml. of 10% by weight aqueous sulfuric acid solution and 50 ml. of saturated aqueous sodium bicarbonate solution. The methylene chloride solution was dried over anhydrous magnesium sulfate and evaporated to dryness to yield 0.082 g. of yellow solid. Recrystallization from ether-hexane at 0°C. yielded 2S-hydroxy-4-cyclopentene-1R-acetic acid lactone, m.p. 44°–45°C. An analytical sample of 2S-hydroxy-4-cyclopentene-1R-acetic acid lactone m.p. 45°–46°C. was obtained by an additional recrystallization from ether-hexane at 0°C.

EXAMPLE 14

To a solution of 0.142 g. (0.0010 mole) of 2S-hydroxy-4-cyclopentene-1S-acetic acid and 1 ml. of pyridine at 0°C. was added dropwise 0.115 g. (0.0010 mole) of methanesulfonyl chloride in 1 ml. of pyridine and the mixture was stirred for 1 hour at 0°C. and 18 hours at room temperature to form a solution containing 2S-methylsulfonyloxy-4-cyclopentene-1S-acetic acid.

A total of 0.5g. of ice was added and the mixture was stirred for 4 hours at room temperature. The mixture was poured into 50 ml. of brine and was extracted with 3 × 50 ml. of methylene chloride. The methylene chloride layers were washed with 50 ml. of 10% by weight aqueous sulfuric acid solution and 50 ml. of saturated aqueous sodium bicarbonate solution. The methylene chloride solution was dried over anhydrous magnesium sulfate and evaporated to dryness to yield 0.078 g. of a semisolid. Two recrystallizations from ether-hexane at 0°C. yielded 2R-hydroxy-4-cyclopentene-1S-acetic acid lactone, m.p. 45°–46°C.

EXAMPLE 15

A mixture of 0.192 g. (0.00150 mole) of 2R-(2-hydroxyethyl-3-cyclopentene-1S-ol, 5 ml. of methylene chloride, and 0.40 g. of sodium bicarbonate was cooled to 0°C. and 0.335 g. (0.00165 mole) of m-chloroperbenzoic acid (purity of 85% by weight) in 3 ml. of methylene chloride was added dropwise. The mixture was stirred at 0°C. for 0.5 hour and at room temperature for 18 hours in the dark.

The mixture was diluted with 50 ml. of ether and this solution was washed with 3 × 50 ml. of water. The water layers were combined and concentrated to dryness to yield 0.224 g. of a colorless oil.

The oil was purified by column chromatography on 15 g. of silica gel (0.05–0.20 mm). A total of 0.013 g. of impurities were eluted with chloroform. The 2% by volume methanol-chloroform fractions afforded oily 2S-hydroxy-4R,5S-epoxycyclopentane-1S-ethanol; b.p. = 140°C. (0.1 mmHg.).

EXAMPLE 16

A mixture of 0.192 g. (0.00150 mole) of 2S-(2-hydroxyethyl)-3-cyclopentene-1R-ol, 5 ml. of methylene chloride, and 0.40 g. of sodium bicarbonate was cooled to 0°C. and 0.335 g. (0.00165 mole) of m-chloroperbenzoic acid (purity of 85% by weight) in 3 ml. of methylene chloride was added dropwise. The mixture was stirred at 0°C. for 0.5 hour and at room temperature for 18 hours in the dark.

The mixture was diluted with 50 ml. of ether and this solution was washed with 3 × 50 ml. of water. The water layers were combined and evaporated to dryness to yield 0.218 g. of a colorless oil.

The oil was purified by column chromatography on 15 g. of silica gel (0.05–0.20 mm). A total of 0.020 g. of impurities were eluted with chloroform. The 2% by volume methanol-chloroform fractions afforded oily 2R-hydroxy-4S,5R-epoxycyclopentane-1R-ethanol; b.p. = 140°C. (0.1 mmHg.).

EXAMPLE 17

To a solution of 0.070 g. (0.00050 mole) of 1aR,2-,2aS,5,5aS,5bS-hexahydro-4H-oxireno[3,4]cyclopenta[1,2-b]furan-4-one in 5 ml. of toluene at −78°C. was added on 0.60 ml. (0.00088 mole) of 1.47 M diisobutylaluminum hydride in toluene and the reaction mixture was stirred at −78°C. for 3 hours. The reaction mixture was quenched by adding 0.5 ml. of methanol, and was diluted with 5 ml. of saturated aqueous sodium sulfate solution and extracted with 3 × 30 ml. of methylene chloride. The methylene chloride extracts were dried over anhydrous sodium sulfate, and evaporated to dryness to yield crystalline 1aR,2aS,-4,5,5aS,5bS-hexahydro-4-hydroxy-2H-oxireno[3,4]cyclopenta[1,2-b]furan. An analytical sample was obtained by recrystallization from ether-hexane at 0°C. to yield fine colorless needles of the furan; m.p. 65°–66°C.

EXAMPLE 18

To a solution of 0.070 g. (0.00050 mole) of 1aS,2-,2aR,5,5aR,5bR-hexahydro-4H-oxireno[3,4]cyclopenta[1,2-b]furan-4-one in 5 ml. of toluene at -78 degrees centigrade was added 0.60 ml. (0.00088 mole) of 1.47 M diisobutylaluminum hydride in toluene and the reaction mixture was stirred at −78°C. for 3 hours. The reaction mixture was quenched by adding 0.5 ml. of methanol, and was diluted with 5 ml. of saturated aqueous sodium sulfate solution and extracted with 3 × 30 ml. of methylene chloride. The methylene chloride extracts were dried over anhydrous sodium sulfate and evaporated to dryness to yield crystalline 1aS,2aR,4,5-,5aR,5bR-hexahydro-4-hydroxy-2H-oxireno[3,4]cyclopenta1,2-b]furan. An analytical sample was obtained by recrystallization from ether-hexane at 0°C. to yield fine colorless needles of the furan; m.p. 65°–66°C.

EXAMPLE 19

A solution of 0.109 g. (0.000765 mole) of 1aR,-2aS,4,5,5aS,5bS-hexahydro-4-hydroxy-2H-oxireno[3,4]cyclopenta[1,2-b]furan in 2 ml. of methanol was cooled to −25°C. and 0.010 g. of boron trifluoride etherate in 0.5 ml. of methanol was added dropwise. The mixture was stirred for 1.5 hours at −25°C. and 1 hour at 0°C. The reaction was quenched by adding 0.10 g. of solid sodium bicarbonate and stirring for 10 minutes. The mixture was diluted with 25 ml. of methylene chloride, dried over anhydrous magnesium sulfate and evaporated to dryness to yield a colorless oil.

Distillation at 50°–52°C. (0.1 mmHg.) afforded 1aR,-2aS,4,5,5aS,5bS-hexahydro-4R-methoxy-2H-oxireno[3,4]cyclopenta[1,2-b]furan.

EXAMPLE 20

A solution of 0.113 g. (0.000795 mole) of 1aS,-2aR,4,5,5aR,5bR-hexahydro-4-hydroxy-2H-oxireno[3,4]cyclopenta[1,2-b]furan in 2 ml. of methanol was cooled to −25°C. and 0.010 g. of boron trifluoride etherate in 0.5 ml. of methanol was added dropwise. The mixture was stirred for 1.5 hours at −25°C. and 1 hour at 0°C. The reaction mixture was quenched by adding 0.10 g. of solid sodium bicarbonate and stirring for 10 minutes.

The mixture was diluted with 25 ml. of methylene chloride, dried over anhydrous magnesium sulfate and evaporated to dryness to yield a colorless oil.

Distillation at 50°–52°C. (0.1 mmHg.) afforded 1aS,-2aR,4,5,5aR,5bR-hexahydro-4S-methoxy-2H-oxireno[3,4]cyclopenta[1,2-b]furan.

EXAMPLE 21

A mixture of 9.35 ml. (0.0140 mole) of 1.5 M butyllithium in hexane, 1.16 g. (0.0070 mole) of 1,3-bis(-methylthio-2-methoxypropane, 1.41 g. (0.0140 mole) of diisopropylamine and 15 ml. of tetrahydrofuran was stirred at −78°C. for 1 hour and at −10°C. for 16 hours to generate a dark red solution of 1,3-bis(methylthio)allyllithium. This solution was recooled to −78°C. and a solution of 0.994 g. (0.00636 mole) of 1aR,-2aS,4,5,5aS,5bS-hexahydro-4R-methoxy-2H-oxireno[3,4]cyclopenta[1,2-b]furan in 5 ml. of tetrahydrofuran was added dropwise. The mixture was stirred at −78°C. for 5 hours and the reaction was quenched by adding 2 ml. of methanol.

The mixture was poured into 50 ml. of saturated aqueous ammonium chloride and this solution was extracted with 4 × 50 ml. of methylene chloride. The methylene chloride layers were washed with 50 ml. of water, dried over anhydrous magnesium sulfate, and evaporated to dryness to yield a ca. 1:1 parts by weight mixture of 4R-(1,3-bismethylthio-2-propen-1-yl)-3,3aR,4,5,6,6aS-hexahydro-5R-hydroxy-2R-methoxy-2H-cyclopenta[b]furan and 5S-(1,3-bismethylthio-2-propen-1-yl)-3,3aR,4,5,6,6aS-hexahydro-4S-hydroxy-2R-methoxy-2H-cyclopenta[b]furan.

EXAMPLE 22

By the procedure of Example 21, 1aS,2aR,4,5-,5aR,5bR-hexahydro-4S-methoxy-2H-oxireno[3,4]cyclopenta[1,2-b]furan is converted to a ca. 1:1 parts by weight mixture of 4S-(1,3-bismethylthio-2-propen-1-yl)-3aS,4,5,6,6aR-hexahydro-5S-hydroxy-2S-methoxy-2H-cyclopenta[b]furan and 5R-(1,3-bismethylthio-2-propen-1-yl)-3,3aS,4,5,6,6aR-hexahydro-4R-hydroxy-2S-methoxy-2H-cyclopenta[b]furan.

EXAMPLE 23

A ca. 1:1 mixture of 1.78 g. (0.00613 mole) of 4R-(1,3-bismethylthio-2-propen-1-yl)-3,3aR,4,5,6,6aS-hexahydro-5R-hydroxy-2R-methoxy-2H-cyclopenta[b]furan and 5S-(1,3-bismethylthio-2-propen-1-yl)-3,3aR,4,5,6,6aS-hexahydro-4S-hydroxy-2R-methoxy- 2H-cyclopenta[b]furan, 5.0 g. (0.0184 mole) of mercuric chloride, 1.84 g. (0.0184 mole) of calcium carbonate, 80 ml. of acetonitrile and 20 ml. of water was stirred at 50°–55°C. for 4 hours and cooled. The mixture was filtered through diatomaceous earth, poured into 50 ml. of brine and extracted with 3 × 50 ml. of methylene chloride. The methylene chloride layers were washed with 50 ml. of brine, dried over anhydrous magnesium sulfate and evaporated to dryness to yield 1.28 g. of a mixture of products.

The mixture was purified by column chromatography on 45 g. of silica gel (0.05–0.20 mm.).

The later fractions eluted with diethyl ether afforded (3,3aR,4,5,6,6aS-hexahydro-5R-hydroxy-2R-methoxy-2H-cyclopenta[b]furan-4R-yl)-E-acrolein.

EXAMPLE 24

The mixture produced in Example 22 was treated by the procedure of Example 23 to produce (3,3aS,4,5,6,-6aR-hexahydro-5S-hydroxy-2S-methoxy-2H-cyclopenta[b]furan-4S-yl)-E-acrolein.

EXAMPLE 25

To a solution of 0.54 g. (0.00254 mole) of (3,3aR,4,5,6,6aS-hexahydro-5R-hydroxy-2R-methoxy-2H-cyclopenta[b]furan-4R-yl)-E-acrolein in 12 ml. of tetrahydrofuran at −25°C. was added 6.0 ml. (0.0066 mole) of 1.1 M n-pentyllithium in pentane and the mixture was stirred at −25°C. for 1 hour and at 0°C. for 1 hour. The mixture was poured into 50 ml. of saturated aqueous ammonium chloride and extracted with 3 × 50 ml. of methylene chloride. The methylene chloride extracts were washed with 50 ml. of brine, dried over anhydrous magnesium sulfate, and evaporated to dryness to yield 0.70 g. of ca. 1:1 parts by weight of mixture of products.

The mixture was purified by column chromatography on 30 g. of silica gel (0.05–0.20 mm). The early diethyl ether fractions afforded 1-(3,3aR,4,5,6,6aS-hexahydro-5R-hydroxy-2R-hydroxy-2R-methoxy-2H-cyclopenta[b]furan-4R-yl)-1E-octen-3R-ol.

The later diethyl ether fractions yielded 1-(3,3aR,4,5,6,6aS-hexahydro-5R-hydroxy-2R-methoxy-2H-cyclopenta[b]furan-4R-yl)-1E-octen-3S-ol.

EXAMPLE 26

The compound (3,3aS,4,5,6,6aR-hexahydro-5S-hydroxy-2S-methoxy-2H-cyclopenta[b]furan-4S-yl)-E-acrolein was treated in the manner of Example 25 and separated by the procedure of Example 25 to yield 1-(3,3aS,4,5,6,6aR-hexahydro-5S-hydroxy-2S-methoxy-2H-cyclopenta[b]furan-4S-yl)-1E-octen-3S-ol and 1-(3,3aS,4,5,6,6aR-hexahydro-5S-hydroxy-2S-methoxy-2H-cyclopenta[b]furan-4S-yl)-1E-octen-3R-ol.

EXAMPLE 27

To a solution of 0.27 g. (0.00095 mole) of 1-(3,3aR,4,5,6,6aS-hexahydro-5R-hydroxy-2R-methoxy-2H-cyclopenta[b]furan-4R-yl)-1E-octen-3S-ol, 4 ml. of acetonitrile and 1 ml. of water was added dropwise 1 ml. of 0.1 N aqueous hydrochloric acid and the mixture was stirred at room temperature for 2 hours. The solution was poured into 50 ml. of brine and extracted with 3 × 50 ml. of methylene chloride. The methylene chloride extracts were washed with 50 ml. of brine, dried over anhydrous magnesium sulfate, and evaporated to dryness to give of 1-(2,5R-dihydroxy-3,3aR,4,5,6,6aS-hexahydro-2H-cyclopenta[b] furan-4R-yl)-1E-octen-3S-ol.

EXAMPLE 28

1-(3,3aS,4,5,6,6aR-hexahydro-5S-hydroxy-2S-methoxy-2H-cyclopenta[b]furan-4S-yl)-1E-octen-3R-ol is converted by the procedure of Example 27 to 1-(2,5S-dihydroxy-3,3aS,4,5,6,6aR-hexahydro-2H-cyclopenta[b]furan-4S-yl)-1E-octen-3R-ol.

EXAMPLE 29

A mixture of 0.25 g. (0.000925 mole) of 1-(2,5R-dihydroxy-3,3aR,4,5,6,6aS-hexahydro-2H-cyclopenta[b]furan-4R-yl)-1E-octen-3S-ol, 2.05 g. (0.00463 mole) of (4-carboxybutyl)triphenylphosphonium bromide, 30 ml. of dimethyl sulfoxide and 0.108 g. (0.00450 mole) of sodium hydride was stirred at 45°–50°C. for 4 hours and cooled.

The mixture was poured into 100 ml. of saturated aqueous ammonium chloride and the solution was extracted with 4 × 50 ml. of methylene chloride. The methylene chloride layers were washed with 50 ml. of brine, dried over anhydrous magnesium sulfate and evaporated to dryness under high vacuum to give 0.36 g. of a mixture of products. The mixture was dissolved in 100 ml. of methylene chloride and the solution was washed with 2 × 25 ml. of ice cold saturated aqueous sodium bicarbonate solution. The aqueous layers were combined, cooled to 0°C. and cautiously acidified with excess 2 N aqueous sulfuric acid. The solution was saturated with excess sodium chloride and was extracted with 4 × 50 ml. of methylene chloride. The methylene chloride layers were washed with 50 ml. of brine, dried over anhydrous magnesium sulfate, and evaporated to dryness to yield of oily naturally occurring (+)-prostaglandin $F_{2\alpha}$ $[\alpha]_n^{25} = +22.4°$ (tetrahydrofuran).

EXAMPLE 30

1-(2,5S-dihydroxy-3,3aS,4,5,6,6aR-hexahydro-2H-cyclopenta[b]furan-4S-yl)-1E-octen-3R-ol is converted by the procedure of Example 29 to an optically active antipode of prostaglandin $F_{2\alpha}$ $[\alpha]_n^{25} = -23.0°$ (tetrahydrofuran).

EXAMPLE 31

By the procedure of Examples 27 and 29, the compound of 1-(3,3aR,4,5,6,6aS-hexahydro-5R-hydroxy-2R-methoxy-2H-cyclopenta [b] furan-4R-yl)-1E-octen-3R-ol is converted to 15-epi-prostaglandin $F_2$ $_\alpha$ via the intermediate 1-(2,5R-dihydroxy-3,3,R,4,5,6,6aS-hexahydro-2H-cyclopenta [b] -furan-4R-yl)-1E-octen-3R-ol. The oily 15-epi-prostaglandin $F_{2\alpha}$ exhibits an optical rotation of $[\alpha]_n^{25} = +11.2°$ (tetrahydrofuran).

EXAMPLE 32

By the procedure of Examples 27 and 28, the compound 1-(3,3aS,4,5,6,6aR-hexahydro-5S-hydroxy-2S-methoxy-2H-Cyclopenta[b]furan-4S-yl)-1E-octen-3S-ol is converted to the optically active antipode of -15-epi-prostaglandin $F_{2\alpha}$ via the intermediate 1-(2,5S-dihydroxy-3,3aS,4,5,6,6aR hexahydro-2H-cyclopenta [b] -furan-4S-yl)-1E-octen-3S-ol. The oily optically active antipode of -15-epi-prostaglandin $F_{2\alpha}$ exhibits an optical rotation of $[\alpha]_n^{25} = -10.9°$ (tetrahydrofuran).

EXAMPLE 33

To a solution of 1.44 g. (0.0100 mole) of 2S-hydroxy-4R,5S-epoxycyclopentane-1S-ethanol in 50 ml. of toluene was added slowly 22.23 g. (0.100 mole)

of 3S-tert-butyloxy-1-octynyldimethylalane in 200 ml. of toluene and the mixture was stirred at 60°–65°C. for 2 hours and cooled. The mixture was poured into 200 ml. of saturated aqueous ammonium chloride at 0°C. The mixture was extracted with 3 × 200 ml. of methylene chloride. The combined methylene chloride extracts were washed with 200 ml. of brine and dried over anhydrous magnesium sulfate. The solution was concentrated to dryness of of yield of 4R-(2-hydroxyethyl)-5S-(3S-tert-butyloxy-1-octynyl)cyclopentane-1R,3S-diol, $[\alpha]_D^{25} = -41°$ (chloroform).

EXAMPLE 34

By the procedure of Example 33, 2R-hydroxy-4S,5R-epoxycyclopentane-1R-ethanol is converted to 4S-(2-hydroxyethyl)-5R-(3R-tert-butyloxy-1-octynyl)cyclopentane-1S,3R-diol by reaction with 3R-tert-butyloxy-1-octynyldimethylalane, $[\alpha]_D^{25} = +41°$ (chloroform).

EXAMPLE 35

A solution of 2.20 g. (0.00675 mole) of 4R-(2-hydroxyethyl)-5S-(3S-tert-butyloxy-1-octynyl)cyclopentane-1R,3S-diol in 10 ml. of trifluoroacetic acid was stirred at −10°C. for 4 hours. The cold solution was added dropwise to a stirred solution of 50 ml. of ice cold 2 N aqueous sodium hydroxide and the mixture was stirred for 5 minutes.

The solution was evaporated to dryness in vacuo. The residue was triturated twice with 100 ml. portions of boiling tetrahydrofuran. The tetrahydrofuran solutions were filtered free of solids and evaporated to dryness to yield a colorless solid. Recrystallization from ethyl acetate yielded 4R-(2-hydroxyethyl)-5S-(3S-hydroxy-1-octynyl)-cyclopentane-1R,3S-diol; m.p. 93°–94°C.; $[\alpha]_D^{25} = +16°$ (CH$_3$OH).

EXAMPLE 36

By the procedure of Example 35, 4S-(2-hydroxyethyl)-5R-(3R-tert-butyloxy-1-octynyl)cyclopentane-1S,3R-diol is converted to 4S-(2-hydroxyethyl)-5R-(3R-hydroxy-1-octynyl)cyclopentane-1S,3R-diol, m.p. = 93°–94°C.; $[\alpha]_D^{25} = -16°$ (CH$_3$OH).

EXAMPLE 37

To a solution of 1.25 g. (0.0330 mole) of lithium aluminum hydride in 50 ml. of tetrahydrofuran was added 1.80 g. (0.00666 mole) of 4R-(2-hydroxyethyl)-5S-(3S-hydroxy-1-octynyl)cyclopentane-1R,3S-diol in 50 ml. of tetrahydrofuran and the mixture was heated at reflux (65°C.) for 6 hours and cooled. To the solution was added 100 ml. of ether and the solution was cooled to 0°C. A total of 2.5 ml. of water was added dropwise followed by 2.0 ml. of 10% by weight aqueous sodium hydroxide and the mixture was stirred for 2 hours. The mixture was filtered and the solids were triturated with 3 × 50 ml. of methylene chloride. The ether and methylene chloride layers were combined, and dried over anhydrous magnesium sulfate. The solution was evaporated to dryness to yield 4R-(2-hydroxyethyl)-5R-(3S-hydroxy-1E-octenyl)cyclopentane-1R,3S-diol, $[\alpha]_D^{25} = +25°$ (CH$_3$OH).

EXAMPLE 38

By the procedure of Example 37, 4S-(2-hydroxyethyl)-5R-(3R-hydroxy-1-octynyl)cyclopentane-1S,3R-diol is converted to 4S-(2-hydroxyethyl)-5S-(3R-hydroxy-1E-octenyl)cyclopentane-1S,3R-diol, $[\alpha]_D^{25} = -25°$ (CH$_3$OH).

EXAMPLE 39

To a solution of 1.76 g. (0.00647 mole) of 4R-(2-hydroxyethyl)-5R-(3S-hydroxy-1E-octenyl)cyclopentane-1R,3S-diol in 15 ml. of pyridine at 0°C. was added 1.81 g. (0.00650 mole) of triphenylmethyl chloride in 10 ml. of pyridine and the mixture was stirred at 0°C. for 2 hours and at room temperature for 16 hours.

The mixture was poured into 50 ml. of saturated brine and the solution was extracted with 3 × 50 ml. of methylene chloride. The methylene chloride layers were washed with 2 × 50 ml. of 10% by weight aqueous sulfuric acid, 50 ml. of saturated aqueous sodium bicarbonate solution and 50 ml. of saturated brine. The solution was then dried over anhydrous magnesium sulfate and evaporated to dryness to yield 5R-(3S-hydroxy-1E-octenyl)-4R-(2-trityloxyethyl)cyclopentane-1R,3S-diol, m.p. = 107°–110°C., $[\alpha]_D^{25} = -20°$ (CHCl$_3$).

EXAMPLE 40

By the procedure of example 39, 4S-(2-hydroxyethyl)-5S-(3R-hydroxy-1E-octenyl)cyclopentane-1S,3R-diol is converted to 5S-(3R-hydroxy-1E-octenyl)-4S-(2-trityloxyethyl)cyclopentane-1S,3R-diol, m.p. = 107°–110°C., $[\alpha]_D^{25} = +20°$ (CHCl$_3$).

EXAMPLE 41

To a mixture of 2.80 g. (0.00545 mole) of 5R-(3S-hydroxy-1E-octenyl)-4R-(2-trityloxyethyl)cyclopentane-1R,3S-diol and 20 ml. of pyridine at 0°C. was added dropwise 2.29 g. (0.02180 mole) of acetic anhydride (97% pure) in 5 ml. of pyridine and the mixture was stirred at 0°C. for 2 hours and 16 hours at room temperature.

The mixture was poured into 50 ml. of water and extracted with 3 × 50 ml. of methylene chloride. The methylene chloride layers were washed with 2 × 50 ml. of 10% by weight aqueous sulfuric acid, 50 ml. of saturated aqueous sodium bicarbonate solution and 50 ml. of saturated brine. The solution was dried over anhydrous magnesium sulfate and evaporated to dryness to give 5R-(3S-acetoxy-1E-octenyl)-4R-(2-trityloxyethyl)cyclopentane-1R,3S-diol diacetate, $[\alpha]_D^{25} = +12°$ (CHCl$_3$).

EXAMPLE 42

By the procedure of Example 41, 5S-(3R-hydroxy-1E-octenyl)-4S-(2-trityloxyethyl)cyclopentane-1S,3R-diol was converted to 5S-(3R-acetoxy-1E-octenyl)-4S-(2-trityloxyethyl)cyclopentane-1S,3R-diol diacetate, $[\alpha]_D^{25} = -12°$ (CHCl$_3$).

EXAMPLE 43

A mixture of 3.12 g (0.00487 mole) of 5R-(3S-acetoxy-1E-octenyl)-4R-(2-trityloxyethyl)cyclopentane-1R,3S-diol diacetate, 45 ml of acetic acid, and 5 ml of water was stirred at room temperature for 34 hours. The mixture was poured into 100 ml of water and was extracted with 3 × 75 ml of ethyl acetate. The ethyl acetate solution was washed with 2 × 100 ml of ice cold 10% by weight aqueous sodium hydroxide solution, 50 ml of water and 50 ml of saturated brine. The ethyl acetate solution was dried over anhydrous magnesium sulfate and evaporated to dryness. The residue was triturated with 4 × 50 ml of petroleum ether (bp 30°–60°C.) and the petroleum ether solution was evaporated to dryness to give 5R-(3S-acetoxy-1E- octenyl)-4R-(2-hydroxyethyl)cyclopentane-1R,3S-diol diacetate, $[\alpha]_D^{25} = +1°$ (CHCl$_3$).

EXAMPLE 44

By the procedure of Example 43, 5S-(3R-acetoxy-1E-octenyl)-4S-(2-trityloxyethyl)cyclopentane-1S,3R-diol diacetate was converted to 5S-(3R-acetoxy-1E-octenyl)-4S-(2-hydroxyethyl)cyclopentane-1S,3R-diol diacetate, $[\alpha]_D^{25} = -1°$ (CHCl$_3$).

EXAMPLE 45

To a rapidly stirred solution of 11.70 g (0.04520 mole) of dipyridine chromium (VI) oxide in 250 ml of methylene chloride was added 1.80 g (0.00452 mole) of 5R-(3S-acetoxy-1E-octenyl)-4R-(2-hydroxyethyl)-cyclopentane-1R,3S-diol diacetate in 10 ml of methylene chloride and the mixture was stirred at room temperature for 20 minutes.

The orange-brown solution was decanted from the solid precipitate and was eluted through a column of 50 g of silica gel (0.50–0.20 mm) with methylene chloride. The appropriate column chromatography fractions were combined and evaporated to dryness to yield 2R-(3S-acetoxy-1E-octenyl)-3R,5S-diacetoxy-1R-cyclopentane acetaldehyde, $[\alpha]_D^{25} = +13°$ (CHCl$_3$).

EXAMPLE 46

By the procedure of Example 45, 5S-(3R-acetoxy-1E-octenyl)-4S-(2-hydroxyethyl)cyclopentane-1S,3R-diol diacetate was converted to 2S-(3R-acetoxy-1E-octenyl)-3S,5R-diacetoxy-1S-cyclopentaneacetaldehyde, $[\alpha]_D^{25} = -13°$ (CHCl$_3$).

EXAMPLE 47

A mixture of 1.30 g (0.00328 mole) of 2R-(3S-acetoxy-1E-octenyl)-3R,5S-diacetoxy-1R-cyclopentaneacetaldehyde, 7.27 g (0.01640 mole) of 4-carboxybutyl)triphenylphosphonium bromide, 75 ml of dimethyl sulfoxide and 0.384 g (0.01600 mole) of sodium hydride was stirred at room temperature for 24 hours.

The mixture was poured into 200 ml of saturated aqueous ammonium chloride. The solution was extracted with 4 × 100 ml of pentane. The pentane layers were washed with 2 × 100 ml of water, dried over anhydrous magnesium sulfate, and evaporated to dryness. The residue was dissolved in 250 ml. of 1:1 parts by volume diethyl ether-pentane and this solution was washed with 2 × 50 ml of ice cold saturated aqueous sodium bicarbonate solution. The aqueous layers were combined, cooled to 0°C. and carefully acidified with excess 2 N aqueous sulfuric acid. The solution was saturated with excess sodium chloride and extracted with 3 × 100 ml of methylene chloride. The methylene chloride layers were washed with 2 × 50 ml of brine, dried over anhydrous magnesium sulfate, and evaporated to dryness to yield 7-[2R-(3S-acetoxy-1E-octenyl)-3R,5S-diacetoxy-1R-cyclopentyl]-5Z-heptenoic acid.

EXAMPLE 48

By the procedure of Example 47, 2S-(3R-acetoxy-1E-octenyl)-3S,5R-diacetoxy-1S-cyclopentaneacetaldehyde was converted to 7-[2S-(3R-acetoxy-1E-octenyl)-3S,5R-diacetoxy-1S-cyclopentyl]-5Z-heptenoic acid.

EXAMPLE 49

A mixture of 0.481 g (0.0010 mole) of 7-[2R-(3S-acetoxy-1E-octenyl)-3R,5S-diacetoxy-1R-cyclopentyl]-5Z-heptenoic acid, 0.660 g (0.0100 mole) of potassium hydroxide (85% pure) and 50 ml of water was stirred for 18 hours at room temperature.

The mixture was cooled to 0°C. and acidified with excess 2 N aqueous sulfuric acid. The solution was saturated with excess sodium chloride and extracted with 4 × 50 ml of ethyl acetate. The ethyl acetate solution was washed with 2 × 50 ml of saturated brine, dried over anhydrous magnesium sulfate and evaporated to dryness to afford naturally occurring (+)-prostaglandin F$_{2\alpha}$ $[\alpha]_D^{25} = +23.2°$ (tetrahydrofuran).

By the above procedure, 7-[2S-(3R-acetoxy-1E-octenyl)-3S,5R-diacetoxy-1S-cyclopentyl]-5Z-heptenoic acid was converted to the optically active antipode of prostaglandin F$_2$ $[\alpha]_D^{25} = -23.0°$ (tetrahydrofuran)

EXAMPLE 50

To a solution of 3.60 g (0.0250 mole) of 2S-hydroxy-4R,5S-epoxycyclopentane-1S-ethanol in 50 ml of toluene was added slowly 55.58 g (0.250 mole) of 3-tert-butyloxy-1-octynyldimethylalane in 450 ml of toluene and the mixture was stirred at 60°–65° for 2 hours and cooled.

The mixture was slowly poured into 500 ml of saturated aqueous ammonium chloride solution at 0° and the mixture was stirred for 0.5 hour. The mixture was extracted with 4 × 250 ml of methylene chloride. The combined methylene chloride extracts were washed with 2 × 250 ml of brine and dried over anhydrous magnesium sulfate. The solution was evaporated to dryness to yield a ca. 1:1 by weight mixture of 4R-(2-hydroxyethyl)-5S-(3S-tert-butyloxy-1-octynyl)cyclopentane-1R,3S-diol and 4R-(2-hydroxyethyl)-5S-(3R-tert-butyloxy-1-octynyl)cyclopentane-1R,3S-diol.

EXAMPLE 51

A solution of 5.20 g (0.0519 mole) of a ca. 1:1 by weight mixture of 4R-(2-hydroxyethyl)-5S-(3S-tert-butyloxy-1-octynyl)cyclopentane-1R,3S-diol and 4R-(2-hydroxyethyl)-5S-(3R-tert-butyloxy-1-octynyl)cyclopentane-1R,3S-diol in 25 ml of trifluoroacetic acid was stirred at −10°C. for 4 hours. The cold solution was added dropwise to a stirred solution of 100 ml of ice cold aqueous 2 N sodium hydroxide solution and this mixture was stirred for 10 minutes.

The solution was saturated with excess sodium chloride and extracted with 4 × 100 ml of methylene chloride. The methylene chloride layers were washed with 2 × 100 ml of saturated brine and dried over anhydrous magnesium sulfate. Evaporation of the solution to dryness yielded a ca. 1:1 by weight mixture of 4R-(2-hydroxyethyl)-5S-(3S-hydroxy-1-octynyl)cyclopentane-1R,3S-diol and 4R-(2-hydroxyethyl)-5S-(3R-hydroxy-1-octynyl)cyclopentane-1R,3S-diol.

EXAMPLE 52

To a stirred solution of 2.88 g (0.0760 mole) of lithium aluminum hydride in 150 ml of tetrahydrofuran at 0°C. was added 4.10 g (0.0152 mole) of a ca. 1:1 by weight mixture of 4R-(2-hydroxyethyl)-5S-(3S-hydroxy-1-octynyl)cyclopentane-1R,3S-diol and 4R-(2-hydroxyethyl)-5S-(3R-hydroxy-1-octynyl)cyclopentane-1R,3S-diol in 100 ml. of tetrahydrofuran and the mixture was heated at reflux 65°C. for 6 hours and cooled. To this solution was added 250 ml. of diethyl ether and the solution was cooled to 0°C. A total of 5.75 ml. of water was added dropwise followed by 4.60 ml. of 10 percent by weight aqueous sodium hydroxide solution and the mixture was stirred for 2 hours. The mixture was filtered and the solids were triturated with 3 × 100 ml. of methylene chloride. The ether and methylene chloride layers were combined, and dried over anhydrous magnesium sulfate. The solution was evaporated to dryness to yield a ca. 1:1 parts by weight mixture of 4R-(2-hydroxyethyl)-5R-(3S-hydroxy-1E-octenyl)cyclopentane-1R,3S-diol and 4R-(2-hydroxyethyl)-5R-(3R-hydroxy-1E-octenyl)cyclopentane-1R,3S-diol.

EXAMPLE 53

To a solution of 3.82 g (0.0140 mole) of a ca. 1:1 parts by weight mixture of 4R-(2-hydroxyethyl)-5R-(3S-hydroxy-1E-octenyl)cyclopentane-1R,3S-diol and 4R-(2-hydroxyethyl)-5R-(3R-hydroxy-1E-octenyl)cyclopentane-1R,3S-diol in 40 ml of pyridine at 0°C. was added 4.03 g (0.0145 mole) of triphenylmethyl chloride in 20 ml of pyridine and the mixture was stirred at 0°C. for 2 hours and at room temperature for 18 hours.

The mixture was poured into 200 ml of saturated brine and the solution was extracted with 4 × 100 ml of methylene chloride. The methylene chloride layers were washed with 2 × 100 ml of 10% by weight aqueous sulfuric acid, 100 ml of saturated aqueous sodium bicarbonate solution and 100 ml of saturated brine. The solution was dried over anhydrous magnesium sulfate and evaporated to dryness to give a ca. 1:1 parts by weight mixture of 5R-(3S-hydroxy-1E-octenyl)-4R-(2-trityloxyethyl)cyclopentane-1R,3S-diol and 5R-(3R-hydroxy-1E-octenyl)-4R-(2-trityloxyethyl)cyclopentane-1R,3S-diol.

EXAMPLE 54

A mixture of 5.15 g (0.0100 mole) of a ca. 1:1 parts by weight mixture of 5R-(3S-hydroxy-1E-octenyl)-4R-(2-trityloxyethyl(cyclopentane-1R,3S-diol and 5R-(3R-hydroxy-1E-octenyl)-4R-(2-trityloxyethyl)cyclopentane-1R,3S-diol, 8.69 g (0.100 mole) of activated manganese dioxide and 250 ml of methylene chloride was rapidly stirred at room temperature for 18 hours.

The solution was filtred through diatomaceous earth and the solids were triturated with 3 × 50 ml of methylene chloride and filtered. The combined methylene chloride layers were dried over anhydrous magnesium sulfate and evaporated to dryness to yield 5R-(3-oxo-1E-octenyl)-4R-(2-trityloxyethyl)cyclopentane-1R,3S-diol.

EXAMPLE 55

A mixture of 0.256 g (0.00050 mole) of 5R-(3-oxo-1E-octenyl)-4R-(2-trityloxyethyl)cyclopentane-1R,3S-diol in 25 ml of tetrahydrofuran was cooled to −78° and a solution of 0.760 g (0.0040 mole) of lithium tri-sec-butylborohydride in 10 ml of tetrahydrofuran was added dropwise. The mixture was stirred at −78° for 24 hours and was quenched by adding 5 ml of methanol. The mixture was warmed to 0°C. and poured into 100 ml of saturated aqueous ammonium chloride solution. This solution was extracted with 4 × 50 ml of methylene chloride. The methylene chloride layers were washed with 2 × 50 ml of brine, dried over anhydrous magnesium sulfate and evaporated to dryness to yield 3:1 parts by weight mixture of 5R-(3S-hydroxy-1E-octenyl)-4R-(2-trityloxyethyl)cyclopentane-1R3S-diol and 5R-(3R-hydroxy-1E-octenyl)-4R-(2-trityloxyethyl)cyclopentane-1R,3S-diol.

Samples of 5R-(3S-hydroxy-1E-octenyl)-4R-(2-trityloxyethyl)cyclopentane-1R,3S-diol and 5R-(3R-hydroxy-1E-octenyl)-4R-(2-trityloxyethyl)cyclopentane-1R,3S-diol were separated with high pressure liquid-liquid chromotography using a 2 mm × 2 feet column of silica gel and 9:1 parts by volume chloroform-methanol as the solvent system, or by column chromatography on 0.05–0.20 mm silica gel.

EXAMPLE 56

A solution of 0.105 g (0.000495 mole) of (3,3aR,4,5,6,6aS-hexahydro-5R-hydroxy-2R-methoxy-2H-cyclopenta[b]furan-4R-yl)-E-acrolein in 2 ml of pyridine was cooled to 0°C. and a solution of 0.118 g (0.000545 mole) of 4-biphenylcarbonyl chloride in 1 ml of pyridine was added dropwise. The mixture was stirred for 6 hours at 0°C. and was poured into 50 ml of ice water.

The mixture was extracted with 3 × 50 ml of methylene chloride. The methylene chloride layers were washed with 50 ml of 10% by weight aqueous sulfuric acid and 50 ml of saturated aqueous sodium bicarbonate solution, dried over anhydrous magnesium sulfate, and evaporated to dryness to yield [3,3aR,4,5,6,6aS-hexahydro-2R-methoxy-5R-(p-phenylbenzoyloxy)-2H-cyclopenta[b]furan-4R-yl]-E-acrolein.

EXAMPLE 57

To a solution of 0.155 g (0.000394 mole) of [3,3aR,4,5,6,6aS-hexahydro-2R-methoxy-5R-(p-phenylbenzoyloxy)-2H-cyclopenta[b]furan-4R-yl]-E-acrolein in 5 ml of tetrahydrofuran at −25° was added 0.37 ml (0.000406 mole) of 1.1 M n-pentyllithium in pentane and the mixture was stirred at −25° for 4 hours. The cold mixture was added to 50 ml of saturated aqueous ammonium chloride solution and extracted with 3 × 50 ml of methylene chloride. The methylene chloride extracts were washed with 50 ml of brine, dried over anhydrous magnesium sulfate, and evaporated to dryness to yield a ca. 1:1 parts by weight mixture of 1-[3,3aR,4,5,6,6aS-hexahydro-2R-methoxy-5R-(p-phenylbenzoyloxy)-2H-cyclopenta[b]furan4R-yl]-1E-octen-3R-ol and 1-[3,3aR,4,5,6,6aS-hexahydro-2R-methoxy-5R-(p-phenylbenzoyloxy)-2H-cyclopenta[b]furan-4R-yl]-1E-octen-3S-ol.

EXAMPLE 58

A mixture of 0.180 g (0.000388 mole) of a ca. 1:1 parts by weight mixture of 1-[3,3aR,4,5,6,6aS-hexahydro-2R-methoxy-5R-(p-phenylbenzoyloxy)-2H-cyclopenta[b]-furan-4R-yl]-1E-octen-3R-ol and 1-[3,3aR,4,5,6,6aS-hexahydro-2R-methoxy-5R-(p-phenylbenzoyloxy)-2H-cyclopenta[b]furan-4R-yl]-1E-octen-3S-ol, 0.338 g (0.00388 mole) of activated manganese dioxide and 15 ml of methylene chloride was rapidly stirred at room temperature for 24 hours.

The solution was diluted with 85 ml of methylene chloride and was filtered through diatomaceous earth.

The solids were triturated with 2 × 25 ml of methylene chloride and filtered. The combined methylene chloride layers were dried over anhydrous magnesium sulfate and evaporated to dryness to yield 3,3aR,4,5,6,6aS-hexahydro-2R-methoxy-4R-(3-oxo-1E-octenyl)-5R-(p-phenylbenzoyloxy)-2H-cyclopenta[b]furan.

EXAMPLE 59

A mixture of 0.116 g (0.000251 mole) of 3,3aR,4,5,6,6aS-hexahydro-2R-methoxy-4R-(3-oxo-1E-octenyl)-5R-(p-phenylbenzoyloxy)-2H-cyclopenta[b] furan in 15 ml of tetrahydrofuran was cooled to −78°C. and a solution of 0.286 g (0.00150 mole) of lithium tri-sec-butylborohydride in 5 ml of tetrahydrofuran was added dropwise. The mixture was stirred at −78° for 24 hours and was quenched by adding 3 ml of methanol. The mixture was warmed to 0°C. and poured into 50 ml of saturated aqueous ammonium chloride solution. The solution was extracted with 3 × 50 ml of methylene chloride. The methylene chloride layers were washed with 50 ml of saturated brine, dried over anhydrous magnesium sulfate and evaporated to dryness to yield an oil.

The oil was purified by column chromatography on 10 g of silica gel (0.05–0.20 mm). The early fractions eluted with diethyl ether afforded a mixture containing (23%) by weight of the oil of 1-[3,3aR,4,5,6,6aS-hexahydro-2R-methoxy-5R(p-phenylbenzoyloxy)-2H-cyclopenta[b]furan-4R-yl]-1E-octen-3R-ol and the latter ether fractions afforded 70% by weight of the oil of 1-[3,3aR,4,5,6,6aS-hexahydro-2R-methoxy-5R-(p-phenylbenzoyloxy)-2H-cyclopenta[b]furan-4R-yl]-1E-octen-3S-ol.

EXAMPLE 60

A solution of 0.0464 g (0.00010 mole) of 1-[3,3aR,4,5,6,6aS-hexahydro-2R-methoxy-5R-(p-phenylbenzoyloxy)-2H-cyclopenta[b]furan-4R-yl]-1E-octen-3S-ol, 1 ml (0.0010 mole) of 1.0 N aqueous sodium hydroxide solution and 5 ml of methanol were stirred for 16 hours at room temperature.

The solution was poured into 25 ml of brine and extracted with 4 × 25 ml of methylene chloride. The methylene chloride extracts were washed with 50 ml of brine, dried over anhydrous magnesium sulfate, and evaporated to dryness to yield 1-(3,3aR,4,5,6,6aS-hexahydro-5R-hydroxy-2R-methoxy-2H-cyclopenta[b]furan-4R-yl)-1E-octen-3S-ol.

EXAMPLE 61

A mixture of 3.30 g. (0.0122 mole) of 4R-(2-hydroxyethyl)-5R-(3S-hydroxy-1E-octenyl)cyclopentane-1R,3S-diol and 25 ml. of pyridine was cooled to 0°C. and 6.40 g. (0.0610 mole) of 97% by weight acetic anhydride in 5 ml. of pyridine was added dropwise. The mixture was stirred at 0° for 2 hours and 16 hours at room temperature.

The mixture was poured into 50 ml. of water and extracted with 3 × 50 ml. of methylene chloride. The methylene chloride layers were washed with 2 × 50 ml. of methylene chloride. The methylene chloride layers were washed with 2 × 50 ml. of 10% by weight aqueous sulfuric acid, 50 ml. of saturated aqueous sodium bicarbonate solution and 50 ml. of saturated brine. The solution was dried over anydrous magnesium sulfate and evaporated to dryness to give oily 4R-(2-acetoxyethyl)-5R-(3S-acetoxy-1E-octenyl)cyclopentane-1R,3S-diol diacetate.

EXAMPLE 62

A mixture of 2.50 g (0.00567 mole) of 4R-(2-acetoxyethyl)-5R-(3S-acetoxy-1E-octenyl)cyclopentane-1R,3S-diol diacetate, 10 ml. of water, and 90 ml. of tert-butyl alcohol was stirred at 0°C. and 5.67 ml. (0.00567 mole) of 1.0 M aqueous sodium hydroxide solution was added dropwise. The mixture was stirred at 0°C. for 4 hr. and was evaporated to dryness at room temperature. The residue was dissolved in 100 ml. of methylene chloride. This solution was washed with 2 × 50 ml. of water, dried over anhydrous magnesium sulfate, and evaporated to dryness to yield 5R-(3S-acetoxy-1E-octenyl)-4R-(2-hydroxyethyl)cyclopentane-1R,3S-diol diacetate.

EXAMPLE 63

A mixture of 0.256 g. (0.0020 mole) of 2R-(2-hydroxyethyl)-3-cyclopenten-1S-ol in 5 ml. of pyridine was cooled to 0 degrees C. and 0.210 g. (0.0020 mole) of 97% by weight acetic anhydride in 1 ml. of pyridine was added dropwise. The mixture was stirred at 0°C. for 2 hr. and at room temperature for 16 hr.

The solution was poured into 50 ml. of saturated brine and was extracted with 3 × 50 ml. of methylene chloride. The methylene chloride layers were washed with 2 × 50 ml. of 10% by weight aqueous sulfuric acid, 50 ml. of saturated aqueous sodium bicarbonate solution, dired over anhydrous magnesium sulfate, and evaporated to dryness to yield an oil.

The oil was purified by column chromatography on 15 g of silica gel (0.05–0.20 mm). A total of 0.080 g of impurities were eluted with benzene and 2% by volume ethyl acetate in benzene. The 5% by volume ethyl acetate-benzene fractions afforded oily 2R-(2-acetoxyethyl)-3-cyclopenten-1S-ol after distillation; b.p. 85°C. (0.1 mmHg.).

EXAMPLE 64

A mixture of 0.256 g. (0.0020 mole) of 2S-(2-hydroxyethyl)-3-cyclopenten-1R-ol in 5 ml. of pyridine was cooled to 0°C. and 0.210 g. (0.0020 mole) of 97% by weight acetic anhydride in 1 ml. of pyridine was added dropwise. The mixture was stirred at 0°C. for 2 hr. and at room temperature for 16 hr.

The solution was poured into 50 ml. of saturated brine and was extracted with 3 × 50 ml. of methylene chloride. The methylene chloride layers were washed with 2 × 50 ml. of 10% by weight aqueous sulfuric acid, 50 ml. of saturated aqueous sodium bicarbonate solution, dried over anhydrous magnesium sulfate, and evaporated to dryness to yield an oil.

The oil was purified by column chromatography on 15 g. of silica gel (0.05 – 0.20 mm). A total of 0.028 g. of impurities were eluted with benzene and 10% by volume ethyl acetate-benzene. The 25% ethyl acetate-benzene fractions afforded oily 2S-(2-acetoxyethyl)-3-cyclopenten-1R-ol after distillation; b.p. = 85°C. (0.1 mmHg.).

EXAMPLE 65

A mixture of 0.093 g. (0.00050 mole) of 2R-(2-acetoxyethyl)-3R,4S-epoxy-1R-cyclopentanol, 4 ml. of water and 1 ml. (0.0010 mole) of 1.0 N aqueous sodium hydroxide solution was stirred for 16 hours at room temperature.

The excess base was neutralized by adding 1 g. of solid carbon dioxide and stirring the mixture for 10 min. The solution was evaporated to dryness and the residue was triturated with 3 × 25 ml. of methylene chloride. The methylene chloride solution was evaporated to dryness to yield oily [2R-hydroxy-4S,5R-epoxycyclopentane-1R-ethanol](epoxy diol). Distillation at 140°C. (0.1 mmHg.) yielded pure epoxy diol.

EXAMPLE 66

A mixture of 0.093 g. (0.00050 mole) of 2S-(2-acetoxyethyl)-3S,4R-epoxy-1S-cyclopentanol, 4 ml. of water and 1 ml. of (0.0010 mole) of 1.0 N aqueous sodium hydroxide solution was stirred for 16 hours at room temperature. The excess base was neutralized by adding 1 g. of solid carbon dioxide (Dry Ice) and stirring the mixture for 10 min. The solution was evaporated to dryness and the residue was triturated with 3 × 25 ml. of methylene chloride. The methylene chloride solution was evaporated to dryness to yield oily 2S-hydroxy-4R,5S-epoxycyclopentane-1S-ethanol (epoxy diol). Distillation at 140°C. (0.1 mmHg.) yielded pure epoxy diol.

EXAMPLE 67

A mixture of 0.170 g. (0.0010 mole) of 2S-(2-acetoxyethyl)-3-cyclopenten-1R-ol, 4 ml. of methylene chloride and 0.40 g. of anhydrous sodium bicarbonate was cooled to 0 degrees C. and 0.224 g. (0.0011 mole) of m-chloroperbenzoic acid (purity of 85% by weight) in 2 ml. of methylene chloride was added dropwise. The mixture was stirred at 0°C. for 1 hr. and at room temperature for 16 hr. in the dark.

The mixture was diluted with 75 ml. of 1:1 parts by volume ethyl acetatemethylene chlroide and this solution was washed with 2 × 25 ml. of 10% by weight aqueous sodium hydroxide and 2 × 25 ml. of saturated brine. The solution was dried over anhydrous magnesium sulfate and evaporated to dryness to yield oily 2R-(2-acetoxyethyl)-3R,4S-epoxy-1R-cyclopentanol. This product was purified by distillation at 100°C. (0.1 mmHg.).

EXAMPLE 68

A mixture of 0.170 g. of (0.0010 mole) of 2R-(2-acetoxyethyl)-3-cyclopenten-1S-ol, 4 ml. of methylene chloride and 0.40 g. of anhydrous sodium bicarbonate was cooled to 0 degrees C. and 0.224 g. (0.0011 mole) of m-chloroperbenzoic acid (purity of 85% by weight) in 2 ml. of methylene chloride was added dropwise. The mixture was stirred at 0°C. for 1 hr. and at room temperature for 16 hr. in the dark.

The mixture was diluted with 75 ml. of 1:1 parts by volume ethyl acetate-methylene chloride and this solution was washed with 2 × 25 ml. of 10% by weight aqueous sodium hydroxide and 2 × 25 ml. of saturated brine. The solution was dried over anhydrous magnesium sulfate and evaporated to dryness to yield oily 2S-(2-acetoxyethyl)-3S,4R-epoxy-1S-cyclopentanol. This product was purified at 100°C. (0.1 mmHg.) by distillation.

EXAMPLE 69

A solution of cyclopentadienylsodium was prepared from 20.5 g. (0.90 g. at) of sodium metal and 39.6 g. (0.60 mole) of cyclopentadiene at −10°C. in 300 ml. of tetrahydrofuran. The solution was filtered through glass wool and added dropwise to a solution of 91.8 g. (0.60 mole) of methyl bromoacetate and 50 ml. of tetrahydrofuran maintained at −78°C. The cold mixture was stirred at −78°C. for 2.5 hr. then was warmed to −60°C. for 16 hrs. to form a solution of methyl 2,4-cyclopentadiene-1-acetate.

A total of 200 ml. (0.20 mole) of 1M borane in tetrahydrofuran was added dropwise to the reaction mixture which was maintained at −60°C. The mixture was allowed to warm to 0°C. over a 1-hr. period and was stirred at 0°C. for 16 hrs to form racemic tris(trans-2-methoxycarbonylmethyl-3-cyclopenten-1-yl)borane.

A solution of 60 ml. of 3 N aqueous sodium hydroxide solution was added to the reaction mixture (0°C.) followed by the dropwise addition of 60 ml. of 30% by weight hydrogen peroxide in water at 0°C.

A total of 5 g. of sodium bisulfite was added to the mixture followed by 20 g. of sodium chloride. The mixture was then extracted with 2 × 250 ml. of ether. The ether layers were combined and washed with 100 ml. of water and 100 ml. of saturated brine. The solution was dried over anhydrous magnesium sulfate and evaporated to dryness to yield 72.1 g. of an oil. Distillation at 80°–83°C. (0.1 mmHg) yielded racemic methyl trans-2-hydroxy-4-cyclopentene-1-acetate.

EXAMPLE 70

A mixture of 4.60 g. (0.0696 mole) of 85% by weight potassium hydroxide in water, 25 ml. of water, 25 ml. of methanol, and 5.44 g. (0.0348 mole) of racemic methyl trans-2-hydroxy-4-cyclopentene-1-acetate was stirred at room temperature for 48 hr. to form a solution containing racemic sodium trans-2-hydroxy-4-cyclopentene-1-acetate.

The solution was diluted with 50 ml. of water and extracted with 3 × 80 ml. of diethyl ether. The combined ether extracts were washed with 50 ml. of water and discarded. The combined water layers were acidified with an excess of a 1:1 parts by volume concentrated aqueous hydrochloric acid-ice slurry and extracted with 3 × 80 ml. of diethyl ether. The combined ether layers were washed with 50 ml. of water and discarded.

The combined water layers were evaporated to dryness and the solid residue was triturated with 3 × 150 ml. of methylene chloride. The methylene chloride solution was filtered and evaporated to dryness to yield racemic trans-2-hydroxy-4-cyclopentene-1-acetic acid as a solid (m.p. 59°–60°C.).

EXAMPLE 71

To a solution of 1.00 g. (0.00704 mole) of racemic trans-2-hydroxy-4-cyclopentene-1-acetic acid in 5 ml. pf pyridine at 0°C. was added dropwise 0.805 g. (0.00773 mole) of methanesulfonyl chloride and the mixture was stirred at 0°C. for 4 hr. and at room temperature for 48 hr. to form a solution containing racemic trans-2-methylsulfonyloxy-4-cyclopentene-1-acetic acid. To this dark solution was added 0.5 g. of ice and the mixture was stirred for 4 hr.

The mixture was diluted with 50 ml. of water and was extracted with 3 × 50 ml. of methylene chloride. The combined methylene chloride layers were washed with 50 ml. of 10% by weight aqueous sulfuric acid, 50 ml. of saturated aqueous sodium bicarbonate solution and 50 ml. of saturated brine. The solution was dried over anhydrous magnesium sulfate and evaporated to dryness to yield 0.700 g. of a dark oil.

The oil was dissolved in 100 ml. of 1:1 parts by volume methylenechloride-ethyl acetate and was washed with 50 ml. of 10% sodium hydroxide solution, 50 ml. of water, and 50 ml. of saturated brine. The solution was dried over anhydrous magnesium sulfate and evaporated to dryness to yield racemic cis-2-hydroxy-4-cyclopentene-1-acetic acid lactone as an oil; b.p. = 50°–52°C. (0.1 mmHg.).

EXAMPLE 72

To a solution of 0.325 g. (0.0021 mole) of racemic methyl trans-2-hydroxy-4-cyclopentene-1-acetate in 2 ml. of pyridine at 0°C. was added dropwise, 0.260 g. (0.0023 mole) of methanesulfonyl chloride in 0.5 ml. of pyridine. The mixture was stirred for 1 hr. at 0°C. and was poured onto crushed ice. The mixture was diluted with 50 ml. of water and extracted with 3 × 50 ml. of diethyl ether. The combined ether layers were washed with 50 ml. of 10% by weight aqueous sulfuric acid, 50 ml. of saturated sodium bicarbonate solution, and 50 ml. of saturated brine. The solution was then dried over anhydrous magnesium sulfate and evaporated to dryness at room temperature to yield 0.465 g. (94%) of a colorless oil that solidified on standing at −10°C. in the refrigerator.

Recrystallization from ether-hexane at 0°C. yielded a first crop of product, i.e. racemic methyl trans-2-methylsulfonyloxy-4-cyclopentene-1-acetate, m.p. 36°–37°C. Recrystallization of the mother liquor yielded a second crop of product, m.p. 34°–36°C.

An analytical sample was secured by an additional recrystallization from ether-hexane at 0°C. to yield fine colorless needles of product, m.p. 37°–38°C.

EXAMPLE 73

To a solution of 0.290 g. (0.00124 mole) of racemic methyl trans-2-methylsulfonyloxy-4-cyclopentene-1-acetate in 10 ml. of tetrahydrofuran and 4 ml. of water at 0°C. was added dropwise, 1.00 ml. (0.0020 mole) of 2 N sodium hydroxide solution. The two-phased solution was vigorously stirred at 0°C. for 1 hr. and at room temperature for 16 hrs. to form racemic sodium cis-2-hydroxy-4-cyclopentene-1-acetate in admixture with racemic cis-2-hydroxy-4-cyclopentene-1-acetic acid lactone.

The mixture was diluted with 50 ml. of water and was extracted with 3 × 50 ml. of diethyl ether. The ether extracts were combined, washed with 25 ml. of water. The water layers were combined, cooled to 0°C., and acidified with excess 6 N aqueous sulfuric acid. The acidic solution was saturated with sodium chloride and extracted with 3 × 50 ml. of methylene chloride. The methylene chloride and ether layers were combined and washed with 50 ml. of saturated aqueous sodium bicarbonate solution. The solution was then dried over anhydrous magnesium sulfate and evaporated to dryness to yield the product racemic cis-2-hydroxy-4-cyclopentene-1-acetic acid lactone as an oil.

Distillation at 50°–52°C. (0.1 mmHg) afforded the pure lactone product.

EXAMPLE 74

A mixture of 0.760 g. (0.0200 mole) of lithium aluminum hydride, 60 ml. of diethyl ether and 2.48 g. (0.0200 mole) of racemic cis-2-hydroxy-4-cyclopentene-1-acetic acid lactone was stirred at 0°C. for 1 hr. To the solution at 0°C. was added dropwise 1.5 ml. of water followed by 1.2 ml. of 10% by weight aqueous sodium hydroxide solution and the mixture was stirred at 0°C. for 1 hr. The solution was then stirred with 0.50 g. of anhydrous magnesium sulfate for 0.5 hr., diluted with 50 ml. of methylene chloride and filtered. The solid residue was triturated with 2 × 50 ml. of methylene chloride and filtered. The combined filtrate was evaporated to dryness to yield 2.60 g. of a colorless viscous oil.

The oil was purified by column chromatography on 30 g. of silica gel (0.05–0.20 mm). A total of 0.10 g. of impurities was eluted with benzene and 10% by volume ethyl acetate-benzene. The 25% by volume ethyl acetatebenzene fractions afforded as an oil product racemic cis-2-(2-hydroxyethyl)-3-cyclopenten-1-ol.

Distillation at 83°–84°C. (0.1 mmHg) yielded the pure diol product.

EXAMPLE 75

A mixture of 0.256 g. (0.0020 mole) of racemic cis-2-(2-hydroxyethyl)-3-cyclopenten-1-ol, 5ml. of methylene chloride, and 0.20 g. of anhydrous sodium bicarbonate was cooled to 0°C. and 0.447 g. (0.0022 mole) of m-chloroperbenzoic acid (purity 85% by weight) in 5 ml. of methylene chloride was added dropwise. The mixture was stirred at 0°C. for 1 hr. and at room temperature for 18 hr.

The mixture was diluted with 100 ml. of diethyl ether and this solution was washed with 4 × 25 ml. of water. The water layers were combined and evaporated to dryness. The solid residue was triturated with 3 × 25 ml. of hot methylene chloride and filtered. The methylene chloride filtrate was evaporated to dryness to yield 0.300 g. of a colorless oil. The oil was purified by column chromatography on 30 g. of silica gel (0.05 – 0.20 mm). The product racemic all-cis-2-hydroxy-4,5-epoxycyclopentane-1-ethanol was eluted with 2% by volume methanol-chloroform. Distillation at 140°–150°C. (0.1 mmHg.) yielded pure product.

EXAMPLE 76

A mixture of 0.513 g. (0.0040 mole) of racemic cis-2-(2-hydroxyethyl)-3-cyclopenten-1-ol, and 8 ml. of pyridine was cooled to 0°C. and 0.461 g. (0.0044 mole) of acetic anhydride in 2 ml. of pyridine was added dropwise. The mixture was stirred at 0°C. for 1 hr. and for 18 hr. at room temperature.

The solution was poured into 50 ml. of saturated brine and was extracted with 3 × 50 ml. of methylene chloride. The methylene chloride layers were washed with 2 × 50 ml. of 10% by weight aqueous sulfuric acid, 50 ml. of saturated aqueous sodium bicarbonate solution, dried over anhydrous magnesium sulfate, and evaporated to dryness to yield 0.700 g. of an oil.

The oil was purified by column chromatography on 30 g. of silica gel (0.05 – 0.20 mm). A total of 0.078 g. of impurities was eluted with benzene and 10% by volume ethyl acetate-benzene. The 25% by volume ethyl acetate-benzene fractions afforded oily racemic cis-2-(2-acetoxyethyl)-3-cyclopenten-1-ol after distillation; b.p. = 85°C. (0.1 mmHg.).

EXAMPLE 77

A mixture of 0.170 g. (0.0010 mole) of racemic cis-2-(2-acetoxyethyl)-3-cyclopenten-1-ol, 4 ml. of methylene chloride and 0.40 g. of anhydrous sodium bicarbonate was cooled to 0°C. and 0.224 g. (0.0011 mole) of m-chloroperbenzoic acid (purity of 85% by weight) in 2 ml. of methylene chloride was added dropwise. The mixture was stirred at 0°C. for 1 hr. and at room temperature for 18 hr. in the dark.

The mixture was diluted with 75 ml. of 1:1 parts by volume ethyl acetatemethylene chloride and this solution was washed with 2 × 25 ml. of 10% by weight aqueous sodium hydroxide solution and 2 × 25 ml. of saturated brine. The solution was dried over anhydrous magnesium sulfate and evaporated to dryness to yield oily racemic all-cis-2-(2-acetoxyethyl)-3,4-epoxy-1-cyclopentanol. Distillation at 100°–105°C. (0.1 mmHg) yielded the pure cyclopentanol product.

EXAMPLE 78

A solution of 0.093 g. (0.00050 mole) of racemic all-cis-2-(2-acetoxyethyl)-3,4-epoxy-1-cyclopentanol, 4 ml. of water and 1 ml. (0.0010 mole) of 1.0 N aqueous sodium hydroxide solution was stirred overnight at room temperature. The excess base was neutralized by adding 1 g. of solid carbon dioxide (Dry Ice) and stirring the mixture for 10 min. The solution was evaporated to dryness and the residue was triturated with 3 × 25 ml. of methylene chloride. The methylene chloride solution was evaporated to dryness to yield oily all-cis-2-hydroxy-4,5-epoxycyclopentane-1-ethanol; b.p. = 140°–150°C. (0.1 mmHg.).

EXAMPLE 79

By the procedure of Examples 41, 43, 45, 47 and 49, 5R-(3R-hydroxy-1E-octenyl)-4R-(2-trityloxyethyl)cyclopentane-1R,3S-diol was converted to 15-epi-prostaglandin $F_{2\alpha}$ $[\alpha]_D^{25} = +11°$ (tetrahydrofuran) via the following intermediates:

5R-(3R-acetoxy-1E-octenyl)-4R-(2-trityloxyethyl)-cyclopentane-1R,3S-diol diacetate;
5R-(3R-acetoxy-1E-octenyl)-4R-(2-hydroxyethyl)-cyclopentane-1R,3S-diol diacetate;
2R-(3R-acetoxy-1E-octenyl)-3R,5S-diacetoxy-1R-cyclopentaneacetaldehyde; and
7-[2R-(3R-acetoxy-1E-octenyl)-3R,5S-diacetoxy-1R-cyclopentyl]-5Z-heptenoic acid.

EXAMPLE 80

By the procedure of Examples 50, 51, 52, 53 and 54, 2R-hydroxy-4S,5R-epoxycyclopentane-1R-ethanol is converted to 5S-(3-oxo-1E-octenyl)-4S-(2-trityloxyethyl)cyclopentane-1S,3R-diol via the following intermediates:

A mixture of 4S-(2-hydroxyethyl)-5R-(3R-tert-butyloxy-1-octynyl)cyclopentane-1S,3R-diol and 4S-(2-hydroxyethyl)-5R-(3S-tert-butyloxy-1-octynyl)cyclopentane-1S,3R-diol;
A mixture of 4S-(2-hydroxyethyl)-5R-(3R-hydroxy-1-octynyl)cyclopentane-1S,3R-diol and 4S-(2-hydroxyethyl)-5R-(3S-hydroxy-1-octynyl)cyclopentane-1S,3R-diol;
A mixture of 4S-(2-hydroxyethyl)-5S-(3R-hydroxy-1E-octenyl)cyclopentane-1S,3R-diol and 4S-(2-hydroxy-ethyl)-5S-(3S-hydroxy-1E-octenyl)cyclopentane-1S, 3R-diol; and
5S-(3R-hydroxy-1E-octenyl)-4S-(2-trityloxyethyl)-cyclopentane-1S,3R-diol and 5S-(3S-hydroxy-1E-octenyl)-4S-(2-trityloxyethyl)cyclopentane-1S,3R-diol.

EXAMPLE 81

By the procedure of Example 55, the compound 5S-(3-oxo-1E-octenyl)-4S-(2-trityloxyethyl)cyclopentane-1S,3R-diol was converted with a 3:1 parts by weight mixture of the following isomers:

5S-(3R-hydroxy-1E-octenyl)-4S-(2-trityloxyethyl)-cyclopentane-1S,3R-diol and 5S-(3S-hydroxy-1E-octenyl)-4S-(2-trityloxyethyl)cyclopentane-1S,3R-diol.

These isomers were separated and isolated as described in Example 55.

EXAMPLE 82

By the procedure of Examples 41, 43, 45, 47 and 49, 5S-(3S-hydroxy-1E-octenyl)-4S-(2-trityloxyethyl)cyclopentane-1S,3R-diol was converted to an optically active anitpode of 15-epi-prostaglandin $F_{2\alpha}$ $[\alpha]_D^{25} = -11°$ (tetrahydrofuran) via the following intermediates:

5S-(3S-acetoxy-1E-octenyl)-4S-(2-trityloxyethyl)cyclopentane-1S,3R-diol diacetate;
5S-(3S-acetoxy-1E-octenyl)-4S-(2-hydroxyethyl)cyclopentane-1S,3R-diol diacetate;
2S-(3S-acetoxy-1E-octenyl)-3S,5R-diacetoxy-1S-cyclopentaneacetaldehyde; and
7- [2S-(3S-acetoxy-1E-octenyl)-3S,5R-diacetoxy-1S-cyclopentyl] -5Z-heptenoic acid.

EXAMPLE 83

By the procedure of Examples 41, 43, 45, 47 and 49, 5S-(3R-hydroxy-1E-octenyl)-4S-(2-trityloxyethyl)cyclopentane-1S,3R-diol was converted to an optically active antipode of prostaglandin $F_{2\alpha}$ via the following intermediates:

5S-(3R-acetoxy-1E-octenyl)-4S-(2-trityloxyethyl)-cyclopentane-1S,3R-diol diacetate;
5S-(3R-acetoxy-1E-octenyl)-4S-(2-hydroxyethyl)cyclopentane-1S,3R-diol diacetate;
2S-(3R-acetoxy-1E-octenyl)-3S,5R-diacetoxy-1S-cyclopentaneacetaldehyde; and
7- [2S-(3R-acetoxy-1E-octenyl)-3S,5R-diacetoxy-1S-cyclopentyl] -5Z-heptenoic acid.

We claim:
1. An optically active compound of the formula:

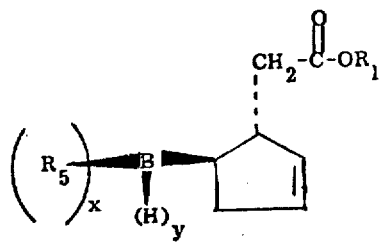

wherein $R_1$ is phenyl, benzyl or lower alkyl; $R_5$ is an optically active organo hydrocarbyl radical; $x$ is an integer from 1 to 2; $y$ is an integer of from 0 to 1 with the proviso that the sum of $x$ and $y$ is 2; or its optically active antipode.

2. The compound of claim 1 wherein said compound is 2R-methoxycarbonylmethyl-3-cyclopenten-1S-yl-bis (1R,2S,3S,5S)-2,6,6-trimethylbicyclo [3.1.1] heptan-3-yl borane.

3. The compound of claim 1 wherein said compound is 2S-methoxycarbonylmethyl-3-cyclopenten-1R-yl-bis (1S,2R,3R,5R)-2,6,6-trimethylbicyclo [3.1.1] heptan-3-yl borane.

* * * * *

UNITED STATES PATENT AND TRADEMARK OFFICE
CERTIFICATE OF CORRECTION

PATENT NO. : 3,933,892
DATED : Jan. 20, 1976
INVENTOR(S) : Naresh Kumar Chadha, John Joseph Partridge, Jr., Milan Radoje Uskokovic It is certified that error appears in the above-identified patent and that said Letters Patent are hereby corrected as shown below:

Column 48, claim 2, lines 54 & 55, (1R,2S,3S,5S)-2,6,6-trimethyl-bicyclo[3,1,1] heptan-2-yl borane should be {(1R,2S,3S,5S)-2,6,6-trimethyl-bicyclo[3.1.1] heptan-3-yl} borane Column 48, claim 3, lines 58 & 59

(1S,2R,3R,5R)-2,6,6-trimethylbicyclo-[3,1,1] heptan-3-yl borane should be

{(1S,2R,3R,5R)-2,6,6-trimethylbicyclo-[3.1.1] heptan-3-yl} borane

Signed and Sealed this

Fifteenth Day of November 1977

[SEAL]

Attest:

RUTH C. MASON
*Attesting Officer*

LUTRELLE F. PARKER
*Acting Commissioner of Patents and Trademarks*